(12) United States Patent
Wadhwani et al.

(10) Patent No.: US 12,396,938 B2
(45) Date of Patent: Aug. 26, 2025

(54) COMPOSITIONS AND METHODS FOR COLORING HAIR

(71) Applicant: L'OREAL, Paris (FR)

(72) Inventors: Mahima Wadhwani, Moonachie, NJ (US); Mohamed Amer Alkahwaji, Hoboken, NJ (US); Emma Howes, Lake Hiawatha, NJ (US)

(73) Assignee: L'OREAL, Paris (FR)

( * ) Notice: Subject to any disclaimer, the term of this patent is extended or adjusted under 35 U.S.C. 154(b) by 89 days.

(21) Appl. No.: 18/459,295

(22) Filed: Aug. 31, 2023

(65) Prior Publication Data

US 2024/0065956 A1  Feb. 29, 2024

Related U.S. Application Data

(60) Provisional application No. 63/402,686, filed on Aug. 31, 2022.

(30) Foreign Application Priority Data

Oct. 11, 2022 (FR) ..................................... 2210418

(51) Int. Cl.
  *A61Q 5/10* (2006.01)
  *A61K 8/41* (2006.01)

(52) U.S. Cl.
  CPC ............... *A61K 8/411* (2013.01); *A61Q 5/10* (2013.01); *A61K 2800/30* (2013.01); *A61K 2800/4324* (2013.01); *A61K 2800/596* (2013.01)

(58) Field of Classification Search
  CPC ............... A61K 8/411; A61K 2800/30; A61K 2800/4324; A61K 2800/596; A61K 8/342; A61K 8/39; A61Q 5/10
  (Continued)

(56) References Cited

U.S. PATENT DOCUMENTS 10,111,816 B2 * 10/2018 Benn ...................... A61K 8/20
  2004/0205904 A1  10/2004 Cotteret et al.
  (Continued)

FOREIGN PATENT DOCUMENTS

EP  2926802 A1  10/2015
  EP  3295924 A1  3/2018
  (Continued)

OTHER PUBLICATIONS

Preliminary Search Report and Written Opinion issued on Apr. 27, 2023 for corresponding French Application No. FR2210418.
(Continued)

Primary Examiner — Eisa B Elhilo
(74) Attorney, Agent, or Firm — POLSINELLI PC

(57) ABSTRACT

The present disclosure relates to hair coloring base compositions and ready-to-use hair coloring compositions comprising 2-methoxymethyl-P-phenylenediamine, an oxidative dye precursor. The hair coloring base composition is mixed with a developer composition to form a ready-to-use hair coloring composition. These compositions are effective for coloring or toning hair. The color imparted to the hair is long-lasting (tenacious), neutralizing, and gentle. Methods for making the composition and methods for coloring hair are also disclosed.

20 Claims, 5 Drawing Sheets
(5 of 5 Drawing Sheet(s) Filed in Color)

(58) Field of Classification Search
USPC .............................................. 8/405, 406, 410
See application file for complete search history.

(56) References Cited

U.S. PATENT DOCUMENTS

| | | |
|---|---|---|
| 2004/0211010 A1 | 10/2004 | Cotteret et al. |
| 2004/0216243 A1 | 11/2004 | Cotteret et al. |
| 2004/0216244 A1 | 11/2004 | Cotteret et al. |
| 2004/0216245 A1 | 11/2004 | Cotteret et al. |
| 2004/0216246 A1 | 11/2004 | Cotteret et al. |
| 2004/0221399 A1 | 11/2004 | Cotteret et al. |
| 2004/0221400 A1 | 11/2004 | Cotteret et al. |
| 2004/0226109 A1 | 11/2004 | Cotteret et al. |
| 2004/0231067 A1 | 11/2004 | Cotteret et al. |
| 2004/0231068 A1 | 11/2004 | Cotteret et al. |
| 2004/0231071 A1 | 11/2004 | Dreher |
| 2004/0250356 A1 | 12/2004 | Cotteret et al. |
| 2006/0037151 A1 | 2/2006 | Lagrange |
| 2006/0112501 A1 | 6/2006 | Dreher et al. |
| 2006/0112502 A1 | 6/2006 | Cotteret et al. |
| 2007/0107142 A1 | 5/2007 | Nguyen et al. |
| 2009/0119852 A1* | 5/2009 | Marsh ..................... A61K 8/34 8/408 |
| 2010/0047201 A1 | 2/2010 | Lalleman et al. |
| 2010/0310489 A1 | 12/2010 | Barba |
| 2011/0035885 A1* | 2/2011 | Zhang ................... A61K 8/494 8/406 |
| 2011/0035886 A1* | 2/2011 | Zhang ..................... A61K 8/44 8/409 |
| 2012/0003167 A1 | 1/2012 | Cavazzuti et al. |
| 2012/0064019 A1 | 3/2012 | Cavazzuti et al. |
| 2012/0100089 A1 | 4/2012 | Barba et al. |
| 2012/0199156 A1 | 8/2012 | Ascione et al. |
| 2012/0210523 A1 | 8/2012 | Lalleman et al. |
| 2012/0276029 A1 | 11/2012 | Ascione et al. |
| 2012/0278997 A1 | 11/2012 | Couroux et al. |
| 2013/0263389 A1 | 10/2013 | Lalleman et al. |
| 2013/0312203 A1 | 11/2013 | Allard et al. |
| 2014/0007359 A1 | 1/2014 | Goget et al. |
| 2014/0013521 A1 | 1/2014 | Goget et al. |
| 2014/0053345 A1 | 2/2014 | Rapold et al. |
| 2014/0068876 A1 | 3/2014 | Rapold et al. |
| 2014/0082855 A1 | 3/2014 | Rapold et al. |
| 2014/0096786 A1 | 4/2014 | Nuzzo et al. |
| 2014/0215728 A1 | 8/2014 | Charrier et al. |
| 2014/0305463 A1 | 10/2014 | Samain et al. |
| 2014/0377199 A1 | 12/2014 | Hercouet et al. |
| 2015/0027483 A1 | 1/2015 | Sabelle et al. |
| 2015/0265525 A1* | 9/2015 | Benn ....................... A61Q 5/10 206/568 |
| 2016/0122286 A1 | 5/2016 | Abel et al. |
| 2018/0177690 A1* | 6/2018 | Boulineau .............. A61K 8/817 |
| 2018/0177704 A1 | 6/2018 | DeGeorge et al. |
| 2019/0060195 A1 | 2/2019 | Elsen et al. |
| 2019/0060196 A1 | 2/2019 | Elsen et al. |
| 2019/0309170 A1 | 10/2019 | Sabelle et al. |
| 2019/0365625 A1 | 12/2019 | Wang et al. |
| 2020/0085714 A1 | 3/2020 | Burckbuchler et al. |
| 2020/0123386 A1 | 4/2020 | Blais et al. |
| 2020/0276102 A1 | 9/2020 | Fadli et al. |
| 2020/0346838 A1 | 11/2020 | Robinson et al. |
| 2021/0177717 A1 | 7/2021 | Consoli et al. |
| 2022/0062142 A1 | 3/2022 | Henry |

FOREIGN PATENT DOCUMENTS

| | | | |
|---|---|---|---|
| EP | 4005641 A1 | 6/2022 | |
| WO | 2014004451 A2 | 1/2014 | |
| WO | WO 2018053177 A1 * | 3/2018 | ............. A61Q 5/10 |
| WO | 2021067173 A1 | 4/2021 | |
| WO | 2021138257 A1 | 7/2021 | |
| WO | 2022182596 A1 | 9/2022 | |

OTHER PUBLICATIONS

Database GNPD [Online]; Mintel; Anonymous: "Permanent Hair Color", 2021 XP093016699.
Database GNPD [Online]; Mintel; Anonymous: "Permanent Creme Hair Colour", 2019 XP093016701.
Katiuscia Grevalcuore et al.; "Hair Care Composition," Research Disclosure, vol. 671, No. 47, 2020, p. 286 XP007148158.

* cited by examiner

Control hair is untreated hair. No product has been applied. BL7X2 – Level 7 hair that has been bleached twice. Goat – Goat hair.

Comparative Tenacity Study for 2-Methoxymethyl-P-Phenylenediamine Vs. Toluene-2,5-Diamine (And) Thioglycerin

Control hair is untreated hair. No product has been applied. BL7 – Level 7 hair that has been bleached once. BL7x2 - Level 7 hair that has been bleached twice. YAK – Yak hair Comparative Tenacity Study for 2-Methoxymethyl-P-Phenylenediamine Vs. Toluene-2,5-Diamine (And) Thioglycerin Results on 90% Grey Hair

COMPOSITIONS AND METHODS FOR COLORING HAIR

CROSS-REFERENCE TO RELATED APPLICATIONS

This application claims the benefit of U.S. Ser. No. 63/402,686, filed Aug. 31, 2022, and benefit of French Application No. FR 2210418, filed on Oct. 11, 2022, which are incorporated herein by reference in their entirety.

FIELD OF THE DISCLOSURE

The present disclosure relates to hair coloring base compositions and ready-to-use hair coloring compositions comprising 2-methoxymethyl-P-phenylenediamine, an oxidative dye precursor. Methods for making the compositions and methods for coloring hair are also described.

BACKGROUND

It is known that consumers desire to use cosmetic and care compositions that enhance their appearance, including the appearance of hair, e.g., by changing the color, style, and/or shape of the hair, and/or by imparting various properties to hair, such as shine and conditioning. Many of the known compositions and processes for enhancing the appearance of the hair involve chemical treatments.

The process of changing the color of hair, for example, can involve depositing an artificial color onto the hair which provides a different shade or color to the hair and/or lifting the color of the hair, such as lightening the color of dark hair to lighter shades. The process of lifting the color of hair, also known as lightening (or bleaching), generally requires the use of compositions that include an oxidizing agent. Lightening or lifting (bleaching) the color of the hair is typically evaluated by the variation in tone height before and after the application of a hair color composition to the hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone. Thus, the higher the number, the lighter the shade or the greater the degree of lightening.

In general, hair lightening or color lifting compositions and hair dyeing compositions possess an alkalinity such that these compositions have a pH value of above 7, typically being at pH 9 and above, and generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While this process is effective in altering the color of the hair, these chemical treatments can damage the hair fibers leading to decreased strength of the hair, as well as negatively affecting the sensorial properties of the hair, such as the smoothness, shine, and feel. Thus, to reduce or avoid these drawbacks, the use of new and additional products and treatments for use before, during, or after (or in conjunction with) the hair coloring or lightening processes are needed.

The choice of such products or treatments pose difficulties insofar as they cannot be detrimental to other cosmetic attributes of the product, such as ease and uniformity of application, rheology or viscosity, stability of the compositions, color deposit and target shade formation. They also should not cause undo damage to the hair or result in the appearance of the hair being undesirable. It would therefore be useful to provide the consumer with products and methods that treat the hair, e.g. lift the color of hair and/or deposit color onto hair in an effective manner, while providing other cosmetic advantages such as shine, conditioning, fiber strength, and/or a healthy appearance to the hair, while avoiding or minimizing damage to the hair.

Most types of hair coloring compositions for permanently coloring hair are oxidative hair coloring compositions that use two parts. The first part is a hair coloring base composition that contains oxidative dye precursors (sometimes called "oxidative dyes" or "oxidation dyes") and couplers, which interact with the oxidative dye precursors. The second part is a developer composition containing an oxidizing agent like hydrogen peroxide. The two parts are mixed immediately prior to use to form a ready-to-use hair coloring composition that is "activated." The ready-to-use hair coloring composition is then applied to the hair for coloring or lightening the color of the hair. Ready-to-use hair coloring compositions can be called "active hair coloring compositions." The oxidative dye precursors and oxidizing agents from the active hair coloring compositions (the ready-to-use coloring composition) diffuse into the hair shaft, where color formation takes place through a cascade of chemical reactions. The oxidative dye precursors are oxidized by the oxidizing agents and form reactive intermediates. Couplers, which are relatively stable to oxidizing agents, react with the intermediates resulting in vibrant coloring molecules.

SUMMARY OF THE DISCLOSURE

The hair coloring compositions of the instant case include 2-methoxymethyl-P-phenylenediamine, an important oxidative dye precursor and one or more couplers. The couplers are useful for varying and improving the shades and colors imparted to the hair by the oxidative dye precursors. Additional oxidative dye precursors may also optionally be included but are not required. The hair coloring base composition is combined with a developer composition to derive a ready-to-use hair coloring composition. These unique hair coloring compositions impart surprisingly long-lasting and vibrant colors to hair and unexpected toning and neutralizing effects to the hair. They are also considerably gentle and non-irritating to the skin and are useful for coloring all types of hair.

The hair coloring base compositions of the instant disclosure include one or more surfactants, and typically include a plurality of surfactants. The total amounts of surfactants in the hair coloring base compositions are unusually high. Without wishing to be bound by any particular theory, it is believed that the high amounts of surfactants contribute, at least in part, to the beneficial properties provided by the hair coloring base compositions. For example, the high amounts of surfactants appear to provide a protective influence and improve the durability of color imparted to the hair. Hair treated with the compositions suffers minimal or no damage and the hair coloring or lightening result is surprisingly long-lasting (durable). The artificially colored hair withstands undue fading over time. The hair coloring base compositions typically include:
(a) 2-methoxymethyl-P-phenylenediamine, and optionally one or more additional oxidative dye precursors;
(b) one or more couplers; and
(c) one or more alkalizing agents;
(d) optionally, one or more fatty alcohols;
(e) one or more surfactants and preferably a plurality of surfactants;
(f) one or more water-soluble organic solvents; and
(g) water.

The amount of the one or more surfactants (e), the one or more water-soluble organic solvents (f), and the water (g) are preferably such that when combined, the total amount of (e), (f), and (g) constitutes at least 70 wt. %, preferably at least 75 wt. %, and even more preferably at least 80 wt. %, of the hair coloring base composition, wherein the percentages by weight are based on a total weight of the hair coloring composition.

As already noted, the hair coloring base compositions include high amounts of one or more surfactants, preferably a plurality of surfactants. The one or more surfactants are selected from nonionic surfactants, anionic surfactants, amphoteric surfactants, cationic surfactants, or combinations thereof. The total amount of the one or more surfactant (preferably a plurality of surfactants) will vary but is typically from about 10 to about 40 wt. %, preferably about 15 to about 25 wt. %, more preferably about 18 to about 28 wt. %, based on the total weight of the hair coloring composition.

The hair coloring composition preferably includes a plurality of surfactants, wherein at least one of the plurality of surfactants is a nonionic surfactant. Furthermore, in preferred embodiments, the plurality of surfactants includes one or more nonionic surfactants, one or more anionic surfactants, and optionally, one or more amphoteric surfactants, preferably wherein the plurality of surfactants is in an amount from about 10 to about 40 wt. %, more preferably about 12 to about 35 wt. %, and even more preferably about 14 to about 28 wt. %, based on the total weight of the hair coloring base composition.

Alkalizing agents influence pH but have a variety of other roles in the hair coloring base compositions. Alkalizing agents can be inorganic or organic, but preferably, the hair coloring base compositions include at least one organic alkalizing agent. Nonlimiting examples of organic alkalizing agents include monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. Nonlimiting examples of mineral alkalizing agents include ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures thereof. However, in various embodiments, the hair coloring base composition is free or essentially free from ammonia and/or ammonium ions, and/or ammonium hydroxide.

The hair coloring base compositions are aqueous (contain water). In addition to water, however, the hair coloring compositions typically include one or more water-soluble organic solvents. The combination of the water and the water-soluble organic solvents can be referred to simply as "solvent." Nonlimiting examples of water soluble organic solvents include glycerin, mono-alcohols, polyols (polyhydric alcohols), glycols, and mixture thereof, e.g., glycerin, propylene glycol, butylene glycol, pentylene glycol, dipropylene glycol, hexylene glycol, ethanol, isopropanol, t-butyl alcohol, and mixture thereof.

In various embodiments, hair coloring base composition preferably includes one or more fatty alcohols but in other embodiments, the hair coloring base composition preferably is free or essentially free from fatty alcohols. When present, the fatty alcohols can be selected from those having from 12 to 24 carbon atoms. Nonlimiting examples include cetyl alcohol, stearyl alcohol, cetearyl alcohol, behenyl alcohol, lauryl alcohol, myristic or myristyl alcohol, arachidyl alcohol, lignoceryl alcohol, and mixtures thereof.

Reducing agents are chemical species that lose an electron to another chemical species in a redox chemical reaction. Nonlimiting examples of reducing agents include ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof. In certain embodiments, the hair coloring base compositions include thioglycolic acid, thiolactic acid, salts thereof (e.g., ammonium thiolactate), and mixtures thereof.

In various embodiments, in is preferable that the hair coloring base compositions are free or essentially free from ammonia, ammonium ions, and/or ammonium hydroxide.

The hair coloring base compositions are mixed with a developer composition to form ready-to-use hair coloring compositions having a desired pH. For example, the hair coloring base compositions may be mixed with a developer composition in a weight ratio of about 5:1 to about 1:5, about 3:1 to about 1:3, or about 2:1 to about 1:2.

The hair coloring base compositions and the developer compositions are separately contained prior to mixing and can be provided in a kit. For example, a kit according to the instant disclosure may include one or more hair coloring base compositions and one or more developer compositions, wherein the hair coloring base compositions and the developer compositions are separately contained. The one or more hair coloring base compositions and the one or more developer compositions may be included in separate containers or compartments that are packaged together.

Methods for making a ready-to-use hair coloring compositions and methods for coloring hair with the compositions entail combining the hair coloring base composition with a developer composition to form a ready-to-use hair coloring composition. The ready-to-use hair coloring composition is then applied to hair for a period of time (for processing), for example, for about 1 to about 30 minutes, about 1 to about 20 minutes, or about 1 to about 15 minutes, about 1 to 10 minutes, or amount 1 to 5 minutes. After the period of time lapses, the hair coloring composition are rinsed or cleansed from the hair exposing the newly colored hair. The newly colored hair durably retains its new color, suffers little or no undesirable chemical damage, and the underlying skin is not subjected to burning and stinging commonly associated with various oxidative coloring products and methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Figure 1:
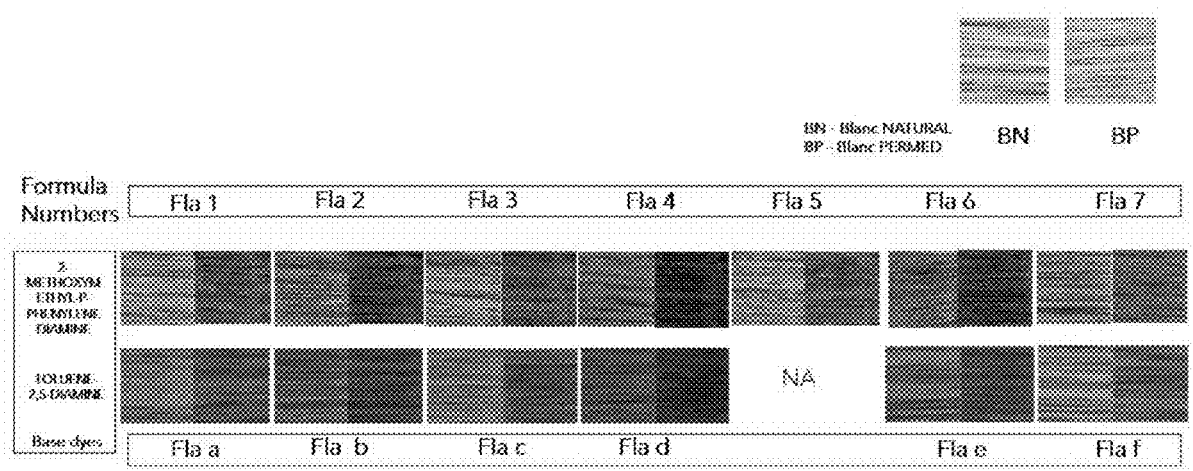
FIG. 1 is a graph showing the color effects of 2-methoxymethyl-p-phenylenediamine provides to hair versus toluene-2,5-diamine (and) thioglycerin.

The hair coloring compositions of the instant case include 2-methoxymethyl-P-phenylenediamine, an important oxidative dye precursor. Additional oxidative dye precursors may also optionally be included but are not required. The hair coloring base composition is combined with a developer composition to derive a ready-to-use hair coloring composition. These unique hair coloring compositions impart surprisingly long-lasting and vibrant colors to hair and unexpected toning and neutralizing effects to the hair. They are also considerably gentle and non-irritating to the skin. In addition, they are useful for coloring all types of hair including hair of the head, eye lashes, eyebrows, and body, beard hair, and mustache hair.

The hair coloring base composition typically includes:
(a) 2-methoxymethyl-P-phenylenediamine, and optionally one or more additional oxidative dye precursors;
(b) one or more couplers; and
(c) one or more alkalizing agents;
(d) optionally, one or more fatty alcohols;
(e) of one or more surfactants;
(f) one or more water-soluble organic solvents; and
(g) water.

The amount of the one or more surfactants (e), the one or more water-soluble organic solvents (f), and the water (g) are preferably such that when combined, the total amount of (e), (f), and (g) constitutes at least 70 wt. %, preferably at least 75 wt. %, and more preferably at least 80 wt. %, of the hair coloring base composition, wherein all percentages by weight are based on a total weight of the hair coloring composition.

The hair coloring base compositions typically include high amounts of one or more surfactants, preferably a plurality of surfactants. For example, the hair coloring base compositions may include one or more nonionic surfactants, anionic surfactants, amphoteric surfactants, cationic surfactants, or a combination thereof. The total amount of the one or more surfactant (preferably a plurality of surfactants) will vary but is typically from about 10 to about 40 wt. %, preferably about 15 to about 25 wt. %, more preferably about 18 to about 28 wt. %, based on the total weight of the hair coloring composition.

In preferred embodiments, the hair coloring composition includes a plurality of surfactants, wherein at least one of the plurality of surfactants is a nonionic surfactant. Furthermore, in a more preferred embodiment, the plurality of surfactants includes one or more nonionic surfactants, one or more anionic surfactants, and optionally, one or more amphoteric surfactants, preferably wherein the plurality of surfactants is in an amount from about 10 to about 40 wt. %, preferably about 15 to about 25 wt. %, more preferably about 18 to about 28 wt. %, based on the total weight of the hair coloring composition. In certain preferred embodiments, at least one of the one or more surfactants (preferably a plurality of surfactants) is an amphoteric surfactant. Preferred amphoteric surfactants include alkyl amphoproprionates, betaines, alkyl sultaines, alkyl amphoacetates, alkyl amphodiacetates, or a combination thereof. Betaines are particularly preferred.

The hair coloring base compositions may be free or essentially free from resorcinol and/or resorcinol derivatives. The hair coloring base compositions may, in some embodiments, be free or substantially free of para-phenylenediamines (other than 2-methoxymethyl-P-phenylenediamine), resorcinol, resorcinol derivatives, or combinations thereof. In some embodiments, the hair coloring base compositions may be free or substantially free of one or more of mineral oil, ammonia, ammonium hydroxide, ammonium thiolactate, para-phenylenediamines (other than 2-methoxymethyl-P-phenylenediamine), resorcinol, resorcinol derivatives, or combinations thereof. In other embodiments, the hair coloring base compositions may be free or substantially free of mineral oil, ammonia, ammonium hydroxide, lactic acid and salts thereof (e.g. ammonium thiolactate), para-phenylenediamines (other than 2-methoxymethyl-P-phenylenediamine), resorcinol, resorcinol derivatives, or combinations thereof.

The hair coloring base compositions are mixed with developer compositions to form ready-to-use hair coloring compositions. The pH for the hair coloring base composition can influence the pH of the ready-to-use hair coloring composition formed by combining the hair coloring base composition with a developer composition. The hair coloring base composition may be mixed with a developer composition in a weight ratio of about 5:1 to about 1:5, about 3:1 to about 1:3, about 2:1 to about 1:2, or about 1:1.

The pH of the hair coloring base composition will vary but is typically from about 6 to about 10.5. In further embodiments, the pH of the hair coloring base composition is from about 6.5 to about 10.5, about 7 to 10.5, about 7.5 to about 10.5, about 7.8 to about 10.5, about 6 to about 10, about 6.5 to about 10, about 7 to about 10, about 7.5 to about 10, or about 7.8 to about 10. The pH of the hair coloring base composition is preferably from about 6.5 to about 10.5, more preferably from about 7 to about 10, and even more preferably from about 7.8 to about 10. In a preferred embodiment, the pH of the hair coloring base composition is from about 7.5 to about 10, more preferably about 7.8 to about 10.

The pH of the ready-to-use hair coloring compositions (formed by combining the hair coloring base composition with a developer composition) will vary but is typically from about 6 to about 10.5. In further embodiments, the pH of the ready-to-use hair coloring composition is from 6 to about 10, about 6 to about 9.5, about 6 to about 9, about 6 to about 8.5, about 6 to about 8, about 6 to about 7.8, about 6.1 to about 10, about 6.1 to about 9.5, about 6.1 to about 9, about 6.1 to about 8.5, about 6.1 to about 8, about 6.1 to about 7.8, about 6.5 to about 10, about 6.5 to about 9.5, about 6.5 to about 9, about 6.5 to about 8.5, about 6.5 to about 8, or about 6.5 to about 7.8. In a preferred embodiment, the ready-to-use hair coloring composition has a pH of about 6 to about 8, more preferably about 6.1 to about 7.8.

(a) 2-Methoxymethyl-P-Phenylenediamine

The hair coloring base compositions include 2-methoxymethyl-P-phenylenediamine, which is an oxidative dye precursor, and optionally one or more additional oxidative dye precursors. Oxidative dye precursors are also referred to as "primary intermediates" or "oxidation bases." Oxidative dye precursors are often colorless or weakly colored compounds, which, when combined with oxidizing products, reactive via oxidative condensation to provide colored species. The shades obtained with oxidative dye precursors may be varied by combining them with one or more couplers.

The total amount of the 2-methoxymethyl-P-phenylenediamine in the hair coloring base composition will vary depending on the desired color and intensity of the hair to be treated. Nonetheless, in various embodiments, the total amount of the 2-methoxymethyl-P-phenylenediamine, is from about 0.001 to about 10 wt. %, about 0.001 to about 8 wt. %, about 0.001 to about 5 wt. %, about 0.001 to about 3 wt. %, about 0.01 to about 10 wt. %, about 0.01 to about 8 wt. %, about 0.01 to about 6 wt. %, or about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, about 0.1 to about 3 wt. %, about 0.2 to about 10 wt. %, about 0.2 to about 8 wt. %, about 0.2 to about 6 wt. %, about 0.2 to about 5 wt. %, or about 0.2 to about 3 wt. %, based on the total weight of the hair coloring base composition. Preferably, the hair coloring base composition includes from about 0.01 to about 6 wt. %, more preferably about 0.05 to about 4 wt. %, even more preferably about 0.1 to about 3 wt. % of the 2-methoxymethyl-P-phenylenediamine, based on the total weight of the hair coloring base composition.

Additional Oxidative Dye Precursors

More specific nonlimiting examples include dimethylpiperazinium aminopyrazolopyridine, 2,3-diaminodihydropyrazolo pyrazolone dimethosulfonate, p-phenylene diamine, 2,5-diaminotoluene, N,N-bis(2-hydroxymethyl)-p-phenylene diamine, paminophenol, salts thereof, etc.

In certain embodiments, in addition to the 2-methoxymethyl-P-phenylenediamine, the hair coloring base composition includes one or more oxidative dye precursors chosen from dimethylpiperazinium aminopyrazolopyridine, 2,3-diaminodihydropyrazolo pyrazolone dimethosulfonate, salts thereof, and combinations thereof.

A more exhaustive but nonlimiting list of useful oxidative dye precursors is described later, under the heading "Oxidative Dye Precursors."

The total amount of the one or more oxidative dye precursors, including 2-methoxymethyl-P-phenylenediamine, will vary depending on the desired color and intensity of the hair to be treated. In various embodiments, the total amount of the one or more oxidative dye precursors, including 2-methoxymethyl-P-phenylenediamine, is from about 0.001 to about 12 wt. %, about 0.001 to about 10 wt. %, about 0.001 to about 8 wt. %, about 0.001 to about 5 wt. %, about 0.01 to about 10 wt. %, about 0.01 to about 8 wt. %, about 0.01 to about 6 wt. %, or about 0.01 to about 5 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.5 to about 12 wt. %, about 0.5 to about 10 wt. %, about 0.5 to about 8 wt. %, about 0.5 to about 6 wt. %, or about 0.5 to about 5 wt. %, based on the total weight of the hair coloring base composition.

The total amount of the one or more oxidative dye precursors other than the 2-methoxymethyl-P-phenylenediamine, will vary but are typically in an amount of about 0.001 to about 10 wt. %, about 0.001 to about 8 wt. %, about 0.001 to about 5 wt. %, about 0.001 to about 3 wt. %, about 0.01 to about 10 wt. %, about 0.01 to about 8 wt. %, about 0.01 to about 6 wt. %, or about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, about 0.1 to about 3 wt. %, about 0.2 to about 10 wt. %, about 0.2 to about 8 wt. %, about 0.2 to about 6 wt. %, about 0.2 to about 5 wt. %, or about 0.2 to about 3 wt. %, based on the total weight of the hair coloring base composition. Preferably, the hair coloring base composition includes from about 0.01 to about 6 wt. %, more preferably about 0.05 to about 4 wt. %, even more preferably about 0.1 to about 3 wt. % of the one or more oxidative dye precursors other than the 2-methoxymethyl-P-phenylenediamine, based on the total weight of the hair coloring base composition.

(b) Couplers

The colors obtained using oxidative dye precursors can be varied by combining them with one or more couplers. Thus, in certain embodiments, the hair coloring base compositions of the instant disclosure preferably include one or more couplers. Non-limiting examples of couplers include aromatic meta-diamines, meta-aminophenols, meta-diphenols, and certain heterocyclic compounds, such as indole compounds. A more exhaustive but non-limiting list of couplers that may be included in the hair coloring base compositions is provided later, under the heading "Couplers." The variety of molecules used as oxidative dye precursors and couplers allow for a wide range of colors to be obtained.

Nonlimiting examples of couplers include of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In a preferred embodiment, the hair coloring base composition includes one or more couplers selected from 2-amino-3-hydroxypyridine, hydroxybenzomorpholine, 2-methyl-5-hydroxyethylaminophenol, 2-methylrescorcinol, 2,4-diaminophenoxy-ethanol HCL, 5-amino-6-chloro-o-cresol, 1-naphthol, or a combination thereof.

The total amount of couplers will vary depending on the desired color of the hair to be treated. Nonetheless, typically, the hair coloring base composition includes about 0.0001 to about 12 wt. % of the one or more couplers, based on the total weight of the hair coloring base composition. In some instances, the total amount of the one or couplers is about 0.001 to about 12 wt. %, about 0.001 to about 10 wt. %, about 0.001 to about 5 wt. %, about 0.001 to about 3 wt. %, about 0.01 to about 10 wt. %, about 0.01 to about 8 wt. %, about 0.01 to about 5 wt. %, about 0.01 to about 3 wt. %, about 0.01 to about 2 wt. %, about 0.01 to about 1 wt. %, about 0.1 to about 10 wt. %, about 0.1 to about 8 wt. %, about 0.1 to about 5 wt. %, about 0.1 to about 3 wt. %, about 0.1 to about 2 wt. %, or about 0.1 to about 1 wt. %, based on the total weight of the hair coloring base composition. Preferably, the hair coloring base composition includes about 0.001 to about 5 wt. %, more preferably about 0.01 to about 4 wt. %, and even more preferably about 0.05 to about 2 wt. % of one or more couplers, based on the total weight of the hair coloring base composition.

Weight Ratio of Oxidative Dye Precursors to Couplers

The weight ratio of the total amount of the oxidative dye precursors (including the 2-methoxymethyl-P-phenylenediamine) to the total amount of the one or more couplers in the hair coloring base composition may be from about 1:2 to about 5:1, about 1:2 to about 4:1, about 1:2 to about 3:1, about 1:2 to about 2:1, about 1:1 to about 5:1, about 1:1 to about 4:1, about 1:1 to about 3:1, or about 1:1 to about 2:1.

In a preferred embodiment, the total amount of the 2-methoxymethyl-P-phenylenediamine to the total amount of the one or more couplers in the hair coloring base composition is from about 1:2 to about 5:1, about 1:2 to about 4:1, about 1:2 to about 3:1, about 1:2 to about 2:1, about 1:1 to about 5:1, about 1:1 to about 4:1, about 1:1 to about 3:1, or about 1:1 to about 2:1. In an even more preferred embodiment, the total amount of the 2-methoxymethyl-P-phenylenediamine to the total amount of the one or more couplers in the hair coloring base composition is from about 1:2 to about 3:1, preferably 1:2 to 2:1, and more preferably from about 1:1 to about 2:1.

(c) Alkalizing Agents

Alkalizing agents in the hair coloring base composition typically have multiple roles in the coloring process. For instance, the one or more alkalizing agents are helpful for obtaining a desired pH. In addition, the one or more alkalizing agents help cause the hair shaft to swell, allowing the small oxidative dye precursors to penetrate the cuticle and cortex more easily. Also, the alkalizing agents can activate one or more oxidizing agents of the developer composition and contribute to the oxidation condensation process.

Non-limiting examples of alkalizing agents include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof.

According to various embodiments, the alkalizing agent may include at least one organic alkalizing agent, at least one mineral alkalizing agent, or combinations thereof. In certain embodiments, the alkalizing agent preferably comprises or consists of one or more organic alkalizing agents. Nonlimiting examples include monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. In a preferred embodiment, the hair coloring base composition includes monoethanolamine, i.e., the alkalizing agent comprises or consists of monoethanolamine.

In further embodiments, the alkalizing agent comprises or is selected from one or more mineral alkalizing agents chosen from ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures thereof. In some embodiments, the alkaline component comprises ammonia and/or ammonium hydroxide but in other embodiments, the alkalizing agent is does not include ammonia and/or ammonia hydroxide, i.e., the hair coloring base compositions are free or essentially free from ammonia and/or ammonia hydroxide.

In some embodiments, the alkalizing agent is selected from one or more organic alkalizing agents and the hair coloring base composition is free or substantially free from mineral alkalizing agents. For example, the alkalizing agent may comprise less than about 0.5 wt. %, less than about 0.4 wt. %, less than about 0.3 wt. %, preferably less than about 0.2 wt. %, less than about 0.1 wt. %, more preferably less than about 0.05 wt. %, and even more preferably less than 0.01 wt. % of mineral alkalizing agents.

In preferred embodiments, the alkalizing agent comprises or consists of at least one organic alkalizing agent and is free or substantially free of ammonia and/or ammonium ions, and/or ammonium-based compounds. Preferably, the alkalizing agent comprises or consists of monoethanolamine. In further embodiments, the alkalizing agent comprises or consists of monoethanolamine and is free or substantially free of ammonia and/or ammonium ions and/or ammonium-based compounds. An "ammonium-based compound" in the context of the instant disclosure is a compound which produces ammonia when in the composition at a particular pH. Examples of such compounds include ammonia and compounds which may be added as ammonium hydroxide and ammonium salts (e.g., simple salts). As ammonium salts, mention may be made of inorganic ammonium salts such as ammonium carbonate, ammonium bicarbonate, ammonium chloride, ammonium nitrate, ammonium sulfate, ammonium phosphate; organic ammonium salts such as ammonium formate, ammonium acetate, and tetramethylammonium hydroxide; and mixtures thereof, The total amount of the one or more alkalizing agents in the hair coloring base compositions will vary but is typically in an amount less than about 3 wt. %, based on the total weight of the hair coloring base composition. In further embodiments, the hair coloring base composition includes less than 3 wt. %, less than 2.5 wt. %, less than 2.2 wt. %, less than 2 wt. %, less than 1.8 wt. %, less than 1.6 wt. %, less than 1.5 wt. %, less than 1.3 wt. %, less than 1.1 wt. %, less than 1 wt. %, based on the total weight of the hair coloring base composition.

As noted previously, the one or more alkalizing agents is preferably monoethanolamine (also referred to as simply "ethanolamine"). The monoethanolamine may be present in the hair coloring base composition in an amount up to about 10 wt. %, depending on a variety of factors, for example, the desired pH of the hair coloring base composition, the ready-to-use hair coloring composition, etc. Accordingly, the amount of monoethanolamine in the hair coloring base composition may be from about 0.001 up to about 10 wt. %, about 0.01 up to about 5 wt. %, about 0.01 to about 4 wt. %, about 0.01 to about 3.8 wt. %, about 0.01 to about 3.5 wt. %, about 0.01 to about 3.2 wt. %, about 0.01 to about 3 wt. %, about 0.01 to about 2.8 wt. %, about 0.01 to about 2.5 wt. %, about 0.01 to about 2.2 wt. %, about 0.01 to about 2 wt. %, about 0.01 to about 1.8 wt. %, about 0.01 to about 1.5 wt. %, about 0.01 to about 1.2 wt. %, about 0.01 to about 1 wt. %, about 0.01 to about 0.8 wt. %, about 0.01 to about 0.5 wt. %, about 0.1 up to about 5 wt. %, about 0.1 to about 4 wt. %, about 0.1 to about 3.8 wt. %, about 0.1 to about 3.5 wt. %, about 0.1 to about 3.2 wt. %, about 0.1 to about 3 wt. %, about 0.1 to about 2.8 wt. %, about 0.1 to about 2.5 wt. %, about 0.1 to about 2.2 wt. %, about 0.1 to about 2 wt. %, about 0.1 to about 1.8 wt. %, about 0.1 to about 1.5 wt. %, about 0.1 to about 1.2 wt. %, about 0.1 to about 1 wt. %, about 0.1 to about 0.8 wt. %, or about 0.1 to about 0.5 wt. %, based on the total weight of the hair coloring base composition. In a preferred embodiment, the hair coloring base composition include about 0.01 to about 5 wt. %, preferably about 0.05 to about 3 wt. %, more preferably about 0.1 to about 2 wt. % of monoethanolamine, based on the total weight of the hair coloring base composition.

(d) Fatty Alcohol

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, comprising from 8 to 40 carbon atoms, preferably 10 to 30 carbon atoms, more preferably 12 to 24 carbon atoms, and even more preferably 14 to 22 carbon atoms.

In a preferred embodiment, the hair coloring base composition includes one or more fatty alcohols.

In a separate preferred embodiment, the hair coloring base compositions is free or essentially free from fatty alcohols.

The fatty alcohols may be liquid or solid. Nonlimiting examples of solid fatty alcohols include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm. The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In preferred embodiments, the one or more fatty alcohols have from 12 to 24 carbon atoms. Specific nonlimiting examples include cetyl alcohol, stearyl alcohol, cetearyl alcohol, behenyl alcohol, lauryl alcohol, myristic or myristyl alcohol, arachidyl alcohol, lignoceryl alcohol, or mixtures thereof. Preferably, the cosmetic composition includes one or more fatty alcohols chosen from cetyl alcohol, stearyl alcohol, behenyl alcohol, oleyl alcohol, and mixtures thereof such as cetylstearyl or cetearyl alcohol.

The liquid fatty alcohols, those containing C10-C34, preferably have branched carbon chains and/or have one or more, preferably 1 to 3 double bonds. They are preferably branched and/or unsaturated (C=C double bond) and contain from 12 to 40 carbon atoms. The liquid fatty alcohols may be represented by: R—OH, wherein R denotes a C12-C24 branched alkyl group or an alkenyl group (comprising at least one C12-C24 double bond C=C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof.

In various embodiments, the hair coloring base composition includes one or more fatty alcohols chosen from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair coloring base compositions preferably includes at least oleyl alcohol.

The total amount of the one or more fatty alcohols, if present, will vary. For example, in various embodiments the hair coloring base composition includes about 0.1 to about 15 wt. % of one or more fatty alcohols, based on the total weight of the hair coloring base compositions. In further embodiments, the hair coloring base composition includes about 0.1 to about 12 wt. %, about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.5 to about 3 wt. %, about 1 to about 15 wt. %, about 1 to about 12 wt. %, about 1 to about 10 wt. %, about 1 to about 8 wt. %, about 1 to about 5 wt. %, about 1 to about 3 wt. %, about 2 to about 15 wt. %, about 2 to about 12 wt. %, about 2 to about 10 wt. %, about 2 to about 8 wt. %, about 2 to about 6 wt. %, about 4 to about 15 wt. %, about 4 to about 12 wt. %, about 4 to about 10 wt. %, about 4 to about 8 wt. %, about 5 to about 15 wt. %, about 5 to about 12 wt. %, or about 5 to about 10 wt. %.

In a preferred embodiment, the hair coloring base composition includes about 0.1 to about 10 wt. %, preferably about 0.5 to about 6 wt. %, more preferably about 1 to about 5 wt. % of the one or more fatty alcohols, based on the total weight of the hair coloring base composition.

In another preferred embodiment, the hair coloring base composition includes about 1 to about 15 wt. %, preferably about 2 to about 12 wt. %, more preferably about 5 to about 10 wt. % of the one or more fatty alcohols, based on the total weight of the hair coloring base composition.

In yet another preferred embodiment, the hair coloring base composition includes less than 5 wt. %, preferably less than 1 wt. %, more preferably less than 0.1 wt. % of the one or more fatty alcohols, and even no fatty alcohols, wherein the weight percentages are based on the total weight of the hair coloring base composition.

(e) Surfactants

In various embodiments, the hair coloring base composition includes one or more surfactants, for example, one or more anionic surfactants, nonionic surfactants, amphoteric surfactants (zwitterionic surfactants), cationic surfactants and/or a mixture thereof. In a preferred embodiment, the hair coloring base composition includes at least one or more nonionic surfactants and preferably also includes one or more anionic surfactants. In certain embodiments, the hair coloring base compositions is preferably free or essentially free from cationic surfactants.

The total amount of the one or more surfactants will vary but is typically about 1 to about 40 wt. %, based on the total weight of the hair coloring base composition. The total amount of the one or more surfactants may be about 1 to about 35 wt. %, about 1 to about 30 wt. %, about 5 to about 40 wt. %, about 5 to about 32 wt. %, about 10 to about 40 wt. %, about 10 to about 35 wt. %, about 10 to about 32 wt. %, about 15 to about 40 wt. %, about 15 to about 35 wt. %, about 15 to about 32 wt. %, about 20 to about 40 wt. %, about 20 to about 32 wt. %, about 20 to about 32 wt. %, or about 25 to about 32 wt. %, based on the total weight of the hair coloring base composition.

If various embodiments, the total amount of the one or more surfactants in the hair coloring base composition is at least 10 wt. %, at least 12 wt. %, at least 15 wt. %, at least 18 wt. %, at least 20 wt. %, at least 21 wt. %, at least 22 wt. %, at least 23 wt. %, or at least 24 wt. %, in each case having an optional maximum amount of up to 30, 35, or 40 wt. %, based on the total weight of the hair coloring base composition.

(i) Nonionic Surfactants

In various embodiments, the hair coloring base composition includes one or more nonionic surfactants. Nonlimiting examples of nonionic surfactants include oxyethylenated amides, oxyethylenated fatty alcohols, and block-copolymer (polycondensate) surfactants of ethylene oxide and of propylene oxide, and a mixture thereof. In a preferred embodiment, the hair coloring base composition includes PEG-4 rapeseedamide (an oxyethylenated amide), deceth-3 (an oxyethylenated fatty alcohol), poloxamer 338 (block-copolymer (polycondensate) surfactants of ethylene oxide and of propylene oxide), or a combination thereof.

Non-limiting examples of nonionic oxyethylenated amides are those of the following formula:

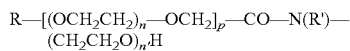

in which:
p denotes 0 or 1,
n denotes a number ranging from 1 to 10 and preferably from 1 to 6,
n' denotes a number ranging from 1 to 100 and preferably from 1 to 60,
R' denotes a hydrogen atom or a $CH_2CH_2OH$ radical and preferably a hydrogen atom, and
R denotes a $C_{10}$-$C_{30}$ and preferably $C_{12}$-$C_{22}$ alkyl or alkenyl radical.

Examples of these compounds include AMIDET A15 sold by the company Kao (INCI name: Trideceth-2 carboxamide MEA), ETHOMID HP 60 sold by the company Akzo Nobel (INCI name: PEG-50 Hydrogenated Palmamide) and AMIDET N sold by the company Kao (INCI name: PEG-4 Rapeseedamide).

In some cases, the hair coloring base compositions includes at least rapeseed amide oxyethylenated with 4 oxyethylene units (PEG-4 rapeseedamide).

Non-limiting examples of fatty alcohols include saturated or unsaturated and linear or branched alcohols comprising from 6 to 30 carbon atoms and preferably from 8 to 30 carbon atoms, for instance, cetyl alcohol, isostearyl alcohol, stearyl alcohol and the mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

Non-limiting examples of oxyethylenated fatty alcohols include those comprising less than 10 OE units, preferably chosen from oxyethylenated derivatives of saturated or unsaturated, linear or branched, preferably linear, $C_8$-$C_{30}$ and preferably $C_{12}$-$C_{22}$ fatty alcohols, for instance cetyl alcohol, oleyl alcohol, oleocetyl alcohol, lauryl alcohol, behenyl alcohol, cetearyl alcohol, stearyl alcohol and isostearyl alcohol, and mixtures thereof.

As oxyethylenated fatty alcohols comprising less than 10 OE units, mention may be made of oxyethylenated fatty alcohols comprising from 2 to 8 and preferably from 2 to 6 OE units, for instance products of addition of ethylene oxide and lauryl alcohol, for instance lauryl alcohol 2 OE (CTFA name: laureth-2), products of addition of ethylene oxide and stearyl alcohol, for instance stearyl alcohol 2 OE (CTFA name: steareth-2), products of addition of ethylene oxide and decyl alcohol, for instance decyl alcohol 3 OE (CTFA name: deceth-3), decyl alcohol 5 OE (CTFA name: deceth-5), products of addition of ethylene oxide and oleocetyl alcohol, for instance oleocetyl alcohol 5 OE (CTFA name: oleoceteth-5), and mixtures thereof. In some instances, deceth-3 may be particularly useful.

Furthermore, non-limiting examples of oxyethylenated fatty alcohols having an average degree of ethoxylation of 2 to 29 are, for example, laureth-2, oleth-2, ceteareth-2, laneth-2, laureth-3, oleth-3, ceteareth-3, laureth-4, oleth-4, ceteareth-4, laneth-4, laureth-5, oleth-5, ceteareth-5, laneth-5, deceth-4, deceth-7, laureth-7, oleth-7, coceth-7, ceteth-7, ceteareth-7, C11-15 pareth-7, laureth-9, oleth-9, ceteareth-9, laureth-10, oleth-10, beheneth-10, ceteareth-10, laureth-12, ceteareth-12, trideceth-12, ceteth-15, laneth-15, ceteareth-15, laneth-16, ceteth-16, oleth-16, steareth-16, oleth-20, ceteth-20, ceteareth-20, laneth-20, steareth-21, ceteareth-23, ceteareth-25, ceteareth-27, and a mixture thereof.

In some cases, the hair coloring base composition includes both at least one nonionic surfactant chosen from oxyethylenated amide and at least one nonionic surfactant chosen from oxyethylenated (OE) fatty alcohol comprising less than 10 OE units, that may be chosen among those described above.

Furthermore, the hair coloring base composition may include one or more nonionic surfactants that is a block-copolymer (polycondensate) surfactant of ethylene oxide and of propylene oxide. The block-copolymer (polycondensate) surfactant of ethylene oxide and of propylene oxide may have a weight-average molecular weight ranging from 1000 to 20000, better from 1500 to 19000, from 2000 to 18000, or from 4000 to 17000.

Mention may be made, as block-copolymer (polycondensate) surfactant of ethylene oxide and of propylene oxide which may be used, of the polyethylene glycol/polypropylene glycol/polyethylene glycol triblock polycondensates sold under the "SYNPERONIC" names, such as "SYNPERONIC PE/F32" (INCI name: Poloxamer 108), "SYNPERONI. PE/F108" (INCI name: Poloxamer 338), "SYNPERONIC PE/L44" (INCI name: Poloxamer 124), "SYNPERONIC PE/L42" (INCI name: Poloxamer 122), "SYNPERONIC PE/F127" (INCI name: Poloxamer 407), "SYNPERONIC PE/F88" (INCI name: Poloxamer 238) or "SYNPERONIC PE/L64" (INCI name: Poloxamer 184), by Croda or also "LUTROL F68" (INCI name: Poloxamer 188), sold by BASF. In some instances, Poloxamer 338 may be particularly useful.

A more exhaustive list of useful nonionic surfactants that may be included in the hair coloring base composition is provided later, under the heading "Nonionic Surfactants."

The total amount of the one or more nonionic surfactants in the hair coloring base composition can vary but is typically about 1 to about 40 wt. %, based on the total weight of the hair coloring base composition. The total amount of the one or more nonionic surfactants may be about 1 to about 35 wt. %, about 1 to about 30 wt. %, about 5 to about 40 wt. %, about 5 to about 32 wt. %, about 10 to about 40 wt. %, about 10 to about 35 wt. %, about 10 to about 32 wt. %, about 15 to about 40 wt. %, about 15 to about 35 wt. %, about 15 to about 32 wt. %, about 20 to about 40 wt. %, about 20 to about 32 wt. %, about 20 to about 32 wt. %, or about 25 to about 32 wt. %, based on the total weight of the hair coloring base composition.

If various embodiments, the total amount of the one or more nonionic surfactants in the hair coloring base composition is at least 10 wt. %, at least 12 wt. %, at least 15 wt. %, at least 18 wt. %, at least 20 wt. %, at least 21 wt. %, at least 22 wt. %, at least 23 wt. %, or at least 24 wt. %, in each case having an optional maximum amount of up to 30, 35, or 40 wt. %, based on the total weight of the hair coloring base composition.

Preferably the hair coloring base composition includes at least 10 wt. % up to 40 wt. %, preferably at least 12 wt. % up to about 35 wt. %, and more preferably at least 14 wt. % up to about 25 wt. % of the one or more nonionic surfactants, based on the total weight of the hair coloring base composition.

(e)(ii) Anionic Surfactant

The term "anionic surfactant" means a surfactant comprising, as ionic or ionizable groups, only anionic groups. These anionic groups may optionally be chosen from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$. Useful cations include alkali metal ions such as sodium or potassium, ammonium ions, or alkanolammonium ions such as monoethanolammonium or triethanolammonium ions.

In various embodiments, the hair coloring base composition includes one or more anionic surfactants. Further, in certain embodiments, the hair coloring base composition includes one or more nonionic surfactants, one or more anionic surfactants, or a mixture thereof. In a preferred embodiment, the hair coloring base composition includes one or more nonionic surfactants and one or more anionic surfactants. The hair coloring base composition may also optionally include one or more amphoteric surfactants, one or more cationic surfactants, or a combination thereof. Nonetheless, in certain embodiments, the hair coloring base composition is preferably free or essentially free from cationic surfactants.

Nonlimiting examples of anionic surfactants include alkyl sulfates, alkyl ether sulfates, acyl isethionates, acyl glycinates, acyl taurates, acyl amino acids, acyl sarcosinates, sulfosuccinates, sulfonates, and a mixture thereof, wherein the alkyl and acyl groups of all these compounds comprise from 6 to 24 carbon atoms. In certain embodiments, however, the hair coloring base composition is free or essentially free from sulfate-based anionic surfactants (e.g., sodium laureth sulfate and sodium lauryl sulfate). Useful non-sulfate-based anionic surfactants include, but are not limited to, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof.

Non-limiting examples of specific acyl isethionates include sodium isethionate, sodium cocoyl isethionate, sodium lauroyl methyl isethionate, and sodium cocoyl methyl isethionate. In some embodiments, sodium cocoyl methyl isethionate is a particularly useful acyl isethionate.

Nonlimiting examples of specific acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some embodiments, sodium lauroyl sarcosinate is preferred.

Non-limiting examples of specific acyl taurates include sodium cocoyl taurate and sodium methyl cocoyl taurate.

Nonlimiting examples of acyl glycinates include sodium cocoyl glycinate, sodium lauroyl glycinate, sodium myristoyl glycinate, potassium lauroyl glycinate, and potassium cocoyl glycinate.

Nonlimiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate.

A nonlimiting but useful example of a $C_{10}$-$C_{24}$ olefin sulfonate that can be used in the instant compositions is sodium $C_{14-16}$ olefin sulfonate.

Nonlimiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, and sodium dialkyl sulfosuccinate.

Nonlimiting examples of alkyl sulfoacetates include, for example, alkyl sulfoacetates such as $C_4$-$C_{18}$ fatty alcohol sulfoacetates and/or salts thereof. A particularly preferred sulfoacetate salt is sodium lauryl sulfoacetate.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and a combination thereof.

Nonlimiting examples of alkyl ether carboxylic acids include ceteareth-2 carboxylic acid, ceteareth-10 carboxylic acid, coceth-7 carboxylic acid, laureth-4 carboxylic acid, laureth-5 carboxylic acid, laureth-6 carboxylic acid, myreth-2 carboxylic acid, myreth-3 carboxylic acid, myreth-4 carboxylic acid, myreth-5 carboxylic acid, myreth-6 carboxylic acid, steareth-2 carboxylic acid, steareth-4 carboxylic acid, steareth-5 carboxylic acid, steareth-6 carboxylic acid, oleth-2 carboxylic acid, oleth-4 carboxylic acid, and mixtures and/or salts thereof.

Nonlimiting examples of additional non-sulfate-based anionic surfactants include saponified oils and neutralized fatty acids. For example, the non-sulfate-based anionic surfactant may be selected from one or more salts of $C_8$-$C_{22}$ saturated or unsaturated fatty acids, such as one or more of sodium cocoate, sodium tallowate, sodium laurate, sodium myristate, sodium stearate, sodium palmate, sodium palm kernelate, sodium olivate, potassium cocoate, potassium tallowate, potassium laurate, potassium myristate, potassium stearate, potassium palmate, potassium palm kernelate, potassium olivate, mono-, di- or tri-ethanolamine cocoate, mono-, di- or tri-ethanolamine tallowate, mono-, di- or tri-ethanolamine laurate, mono-, di- or tri-ethanolamine myristate, mono-, di- or tri-ethanolamine stearate, mono-, di- or tri-ethanolamine palmate, mono-, di- or tri-ethanolamine palm kernelate, and mono-, di- or tri-ethanolamine olivate. In a preferred embodiment, the cleansing composition includes at least one non-sulfate-based anionic surfactant selected from sodium cocoate, sodium tallowate, sodium laurate, sodium myristate, sodium stearate, sodium palmate, sodium palm kernelate, and sodium olivate.

In a preferred embodiment, the hair coloring base composition includes one or more anionic surfactants selected from laureth-5 carboxylic acid, sodium cetearyl sulfate, PPG-5-ceteth-10 phosphate, sodium $C_{14-16}$ olefin sulfonate, or a combination thereof.

The total amount of the one or more anionic surfactants, if present, will vary. In certain embodiments, the hair coloring base composition includes about 0.1 to about 15 wt. % of the one or more anionic surfactants, based on the total weight of the hair coloring base composition. In further embodiments, the hair coloring base composition includes about 0.1 to about 12 wt. %, about 0.1 to about 10 wt. %, about 0.1 to about 8 wt. %, about 0.1 to about 6 wt. %, about 0.5 to about 15 wt. %, about 0.5 to about 12 wt. %, about 0.5 to about 10 wt. %, about 0.5 to about 8 wt. %, about 0.5 to about 6 wt. %, about 1 to about 15 wt. %, about 1 to about 12 wt. %, about 1 to about 10 wt. %, about 1 to about 8 wt. %, about 2 to about 10 wt. %, about 3 to about 8 wt. %, or about 4 to about 7 wt. %, based on the total weight of the hair coloring base composition.

Preferably, the hair coloring base composition includes from about 0.1 to about 15 wt. %, more preferably about 0.5 to about 12 wt. %, even more preferably about 1 to about 12 wt. % of the one or more anionic surfactants, based on the total weight of the hair coloring base composition.

(e)(iii) Amphoteric Surfactants

Nonlimiting examples of amphoteric surfactants include alkyl amphoproprionates, betaines, alkyl sultaines, alkyl amphoacetates, and combinations thereof. Preferably, at least one of the one or more amphoteric surfactants is a betaine.

Nonlimiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, and lauroamphopropionate.

Nonlimiting examples of betaines include coco-betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof. Typically, at least one betaine compound is selected from coco betaine, cocamidopropyl betaine, behenyl betaine, capryl/capramidopropyl betaine, and lauryl betaine. Particularly preferred betaines include coco-betaine, cocamidopropyl betaine, or a combination thereof.

Nonlimiting examples of alkyl sultaines include cocamidopropyl hydroxysultaine and lauryl hydroxysultaine.

A nonlimiting example of an alkyl amphoacetate is sodium or potassium lauroamphoacetate.

The total amount of the one or more amphoteric surfactants in the hair coloring base composition, if present, will vary but is typically from about 0.1 to about 10 wt. %, based on the total weight of the hair coloring base composition. In some embodiments, the total amount of the one or more amphoteric surfactants in the hair coloring base composition is from about 0.1 to about 8 wt. %, about 0.1 to about 5 wt. %, about 0.1 to about 3 wt. %, about 0.5 to about 10 wt. %, about 0.5 to about 8 wt. %, about 0.5 to abut 5 wt. %, about 0.5 to about 3 wt. %, or about 0.5 to about 2 wt. %, based on the total weight of the hair coloring base composition.

(f) Water Soluble Organic Solvent

In various embodiments, the hair coloring base composition includes one or more water-soluble organic solvents (or simply "water-soluble solvents"). The term "water-soluble organic solvent" (or "water-soluble solvent") is interchangeable with the term "water-miscible solvent" and means an organic compound that is liquid at 25° C. and at atmospheric pressure (760 mmHg), and it has a solubility of at least 50% in water under these conditions. In certain embodiments, the one or more water-soluble organic solvents have a solubility of at least 60%, 70%, 80%, or 90% in water at 25° C. and at atmospheric pressure (760 mmHg). Non-limiting examples of water-soluble organic solvents include glycerin, mono-alcohols (for example, $C_{2-8}$ alcohols), polyols, glycols, and a mixture thereof. In certain embodiments, the one or more water-soluble organic solvents are chosen from alcohols such as ethyl alcohol, isopropyl alcohol, propyl alcohol, benzyl alcohol, and phenylethyl alcohol, or glycols or glycol ethers such as monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Further non-limiting but useful examples of water-soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2- pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In various embodiments, the hair coloring base composition includes one or more water-soluble organic solvents chosen from glycols, $C_{1-4}$ alcohols, glycerin, and a mixture thereof; preferably the water-soluble organic solvent is chosen from caprylyl glycol, glycerin, ethanol, isopropyl alcohol, dipropylene glycol, propylene glycol, hexylene glycol, caprylyl glycol, propylene glycol, glycerin, ethanol, and a mixture thereof.

In certain embodiments, the hair coloring base composition includes one or more polyhydric alcohols. Nonlimiting examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the one or more water-soluble organic solvents will vary but is typically an amount from about 0.01 to about 50 wt. %, based on the total weight of the hair coloring base composition. For example, the total amount of water soluble organic solvent may range from about 1% to about 50%, about 2% to about 50%, about 3% to 50%, about 4% to about 50%, about 5% to about 50%, 1% to about 40%, about 2% to about 40%, about 3% to 40%, about 4% to about 40%, about 5% to about 40%, about 1% to about 35%, about 2% to about 35%, about 3% to 35%, about 4% to about 35%, or about 5% to about 35% by weight, relative to the total weight of the composition.

Depending on various factors, the total amount of the water soluble organic solvents in the hair coloring base composition may be from about 1% to about 10%, about 2% to about 8%, about 3% to about 7%, about 15 to about 40 wt. %, about 15 to about 30 wt. %, about 25% to about 45%, about 25% to about 40%, about 25% to about 35%, or about 30% to about 35% by weight, relative to the total weight of the composition.

In a preferred embodiment, higher amounts of water soluble organic solvents are used in the hair coloring base compositions. For example, the hair coloring base compositions may include about 10 to about 40 wt. %, about 10 to about 30 wt. %, about 15 to about 40 wt. %, about 15 to about 30 wt. %, about 18 to about 40 wt. %, about 18 to about 30 wt. %, about 20 to about 40 wt. %, about 20 to about 30 wt. %, or about 20 to about 25 wt. % of the one or more water soluble solvents. Preferably, when higher amounts of water soluble solvents are include, the amount is from about 10 to about 40 wt. %, preferably about 15 to about 35 wt. %, and even more preferably about 20 to about 30 wt. %, based on the total weight of the hair coloring base composition.

In another preferred embodiment, lower amounts of water soluble organic solvents are used in the hair coloring base compositions. For example, the hair coloring base composition may include about 0.1 to about 15 wt. %, preferably about 0.5 to about 10 wt. %, more preferably about 1 to about 5 wt. % of the one or more water soluble organic solvents.

(g) Water

The hair coloring base composition includes varying amounts of water. The amount of water may vary depending on the desired consistency of the product, the amount of water (if any) in a developer composition with which the hair coloring base composition will be mixed, etc. Nonetheless, the total amount of water is typically from about 25 wt. % to about 80 wt. %, based on the total weight of the hair coloring base composition. In further embodiments, the total amount of water in the hair coloring base composition is from about 25 to about 75 wt. %, about 25 to about 70 wt. %, about 25 to about 60 wt. %, about 25 to about 50 wt. %, about 40 to about 75 wt. %, about 40 to about 70 wt. %, about 40 to about 60 wt. %, about 40 to about 50 wt. %, about 50 to about 75 wt. %, about 50 to about 70 wt. %, about 50 to about 60 wt. %, about 60 to about 75 wt. %, or about 60 to about 70 wt. %, based on the total weight of the hair coloring base composition.

If various embodiments, the total amount of water in the hair coloring base composition is at least at least 25 wt. %, at least 30 wt. %, at least 35 wt. %, at least 40 wt. %, at least 45 wt. %, at least 50 wt. %, at least 55 wt. %, at least 60 wt. %, at least 65 wt. % or at least 70 wt. %, in each case having an optional maximum amount of up to 45, 50, 55, 65, 70, or 75 wt. %, based on the total weight of the hair coloring base composition.

In a further embodiment, the hair coloring base compositions include higher amounts of water. For example, from about 50 to about 85 wt. %, about 60 to about 85 wt. %, about 65 to about 85 wt. %, about 70 to about 85 wt. %, about 50 to about 80 wt. %, about 60 to about 80 wt. %, about 65 to about 80 wt. %, about 70 to about 80 wt. %, based on the total weight of the hair coloring base composition.

Total Amounts of Combination of Water and Water Soluble Organic Solvents

The combined amount of water and the one or more water soluble solvents will vary. For instance, if higher amounts of water soluble organic solvents are included in the hair coloring base compositions, lower amounts of water will be needed and vice versa. Nonetheless, combined amount of water and the one or more water soluble solvents may be from 10% to about 95% by weight, relative to the total weight of the hair coloring base composition. For example, the total amount of solvent may range from about 25 to about 90 wt. %, about 20 to about 85 wt. %, about 25 to about 75 wt. %, about 25 to 70 wt. %, about 25 to about 65 wt. %, about 25 to about 60 wt. %, about 30 to about 75%, about 30 to 70 wt. %, about 30 to about 65 wt. %, about 30 to about 60 wt. %, about 30 to about 55 wt. %, about 40 to 75 wt. %, about 40 to about 70 wt. %, about 40 to about 65 wt. %, about 40 to about 60 wt. %, based on the total weight of the hair coloring base composition.

In a preferred embodiment, the combined amount of water and the one or more water soluble solvents is from about 50 to about 80 wt. %, preferably about 55 to about 75 wt. %, more preferably from about 60 to about 75 wt. %, based on the total weight of the hair coloring base composition.

Total Amounts of (e), (f), and (g)

As discussed above, the hair coloring base compositions of the instant disclosure include varying amounts of surfactants, water-soluble organic solvents, water, etc. Nonetheless, in various embodiments, the total amount (the combined amount) of surfactants, water-soluble organic solvents, and water in the hair coloring base composition is from about 60 wt. % to about 95 wt. % based on the total weight of the hair coloring base composition. In further embodiments, the total amount (the combined amount) of surfactants, water-soluble organic solvents, and water in the hair coloring base composition is from about 65 to about 95 wt. %, from about 70 to about 95 wt. %, from about 75 to about 95 wt. %, from about 80 to about 95 wt. %, from about 85 wt. % to about 95 wt. %, from about 60 to about 90 wt. %, from about 65 to about 90 wt. %, from about 70 to about 90 wt. %, from about 75 to about 90 wt. %, from about 80 to about 90 wt. %, or from about 85 to about 90 wt. %, based on the total weight of the hair coloring base composition.

In further embodiments, the total amount (the combined amount) of surfactants, water-soluble organic solvents, and water in the hair coloring base composition is at least 60 wt. %, at least 65 wt. %, at least 70 wt. %, at least 75 wt. %, at least 80 wt. %, or at least 85 wt. %, based on the total weight of the hair coloring base composition.

(h) Reducing Agents

The types of reducing agents that may be included in the hair coloring base compositions can vary. Nonlimiting examples of reducing agents include ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, salts thereof, and mixtures thereof. The salts referred to throughout the disclosure may include salts having a counter-ion such as an alkali metal, alkaline earth metal, or ammonium counterion. This list of counterions, however, is non-limiting. In various embodiments, preferred reducing agents include thiolactic acid, glycolic acid, salts thereof (e.g., ammonium thiolactate), and combinations thereof.

In various embodiments, the one or more reducing agents may be from thiols such as thioglycolic acid or a salt thereof, thiolactic acid or a salt thereof, 3-mercaptopropionic acid, thiomalic acid, 2,3-dimercaptosuccinic acid, cysteine, N-glycyl-L-cysteine, L-cysteinylglycine and also esters and salts thereof, thioglycerol, cysteamine and $C_1$-$C_4$ acyl derivatives thereof, N-mesylcysteamine, N-acetylcysteine, N-mercaptoalkylamides of sugars such as N-(mercapto-2-ethyl) gluconamide, pantetheine, N-(mercaptoalkyl)-Q-hydroxyalkylamides, N-mono- or N,N-dialkylmercapto-4-butyramides, aminomercaptoalkyl amides, N-(mercaptoalkyl) succinamic acids and N-(mercaptoalkyl)succinimides, alkylamino mercaptoalkyl amides, mercaptoalkylamino amides, N-mercaptoalkylalkanediamides, ammonium bisulfite, ammonium sulfite, potassium metabisulfite, potassium sulfite, sodium hydrosulfite, sodium metabisulfite, sodium sulfite, sodium bisulphite, and a mixture thereof. In further embodiments, the hair coloring base composition include one or more reducing agents chosen from thioglycolic acid, thiolactic acid, 3-mercaptopropionic acid, salts thereof, and a combination thereof.

The reducing agent may also be chosen from hydrides such as sodium or potassium borohydride or alkali metal or alkaline-earth metal sulfites or bisulfites; or alternatively from phosphorus derivatives such as phosphines or phosphites. In various embodiments, the one or more reducing agents are chosen from ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, dehydroascorbic acid, a salt thereof, and a mixture thereof.

In a preferred embodiment, the one or more reducing agents are selected from ammonium thiolactate, sodium sulfite, or a combination thereof.

The total amount of the one more reducing agents in the hair coloring base composition may vary but is typically about 0.01 to about 10 wt. %, based on the total weight of the composition. The total amount of the one or more reducing agents may be about 0.01 to about 8 wt. %, about 0.01 to about 5 wt. %, about 0.1 to about 10 wt. %, about 0.1 to about 8 wt. %, about 0.1 to about 5 wt. %, about 0.1 to about 3 wt. %, or about 0.1 to about 2 wt. %, based on the total weight of the hair coloring base composition.

(i) Fatty Compound Other than Fatty Alcohols

In various embodiments, the hair coloring composition may include one or more fatty compounds other than fatty alcohols, preferably one or more non-silicone fatty compounds. The term "non-silicone fatty compound" means a fatty compound that does not containing any silicon atoms (Si). Non-limiting examples of non-silicone fatty compounds include oils, mineral oil, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. Non-limiting examples of fatty acids, fatty alcohol derivatives, and fatty acid derivatives are found in International Cosmetic Ingredient Dictionary, Sixteenth Edition, 2016, which is incorporated by reference herein in its entirety.

In various embodiments, the one or more fatty compounds other than fatty alcohols are liquid fatty compounds, also referred to "oils." "Oil" is used herein to refer to an organic compound other than a fatty alcohols that is insoluble in water at normal temperature (25° C.) and at atmospheric pressure (760 mmHg), i.e. it has a water solubility of less than 5% by weight, or less than 1% by weight, or less than 0.1% by weight. Oils have in their structure a chain of at least two siloxane groups or at least one hydrocarbon chain having at least 6 carbon atoms. Furthermore, oils are generally soluble in organic solvents in the same conditions of temperature and pressure, for example in chloroform, ethanol, benzene or decamethylcyclopentasiloxane.

Furthermore, oils are liquid at ordinary temperature (25° C.) and at atmospheric pressure (760 mmHg). The oils preferably do not contain any carboxylic acid functions, i.e. they do not contain any —COOH or —COO— groups. As described throughout the disclosure fatty alcohols are independent from fatty compounds and oils, i.e., even if a fatty alcohol is present in the compositions of the instant disclosure, the compositions may nonetheless be free or essentially free from fatty compounds of oils (because fatty alcohols are not included in the definition of fatty compounds and oils).

In a preferred embodiment, the hair coloring base composition includes one or more oils, preferably one or more oils of plant origin.

The total amount of the one or more fatty compounds in the hair coloring compositions other than fatty alcohols, if present, will vary. Nonetheless, in various embodiments, the total amount of fatty compounds other than fatty alcohols is from about 0.1 to about 20 wt. %, based on the total weight of the hair coloring composition. In further embodiments, the total amount of fatty compounds is from about 0.01 to about 15 wt. %, about 0.05 to about 10 wt. %, or about 0.1 to about 5 wt. %, based on the total weight of the hair coloring base composition.

The total amount of the one or more oils (a type of fatty compound) in the hair coloring base compositions, if present, will vary. Nonetheless, in various embodiments, the total amount of oil is from about 0.1 to about 18 wt. %, about 0.1 to about 15 wt. %, about 0.1 to about 10 wt. %, about 0.1 to about 5 wt. %, about 0.1 to about 3 wt. %, about 0.1 to about 2 wt. %, based on the total weight of the hair coloring base composition. In further embodiments, the hair coloring compositions not more than 18 wt. % of oils, not more than 15 wt. % or oils, not more than 12 wt. % of oils, not more than 10 wt. % of oils, not more than 8 wt. % of oils, not more than 5 wt. % of oils, not more than 4 wt. % of oils, not more than 3 wt. % of oils, not more than 2 wt. % of oils, not more than 1 wt. % of oil, or may be free or essentially free from oils.

In various embodiments the hair coloring base compositions are free or essentially free from mineral oil, polybutene, hydrogenated polyisobutene, hydrogenated polydecene, polydecene, squalane, petrolatum, petroleum jelly (including liquid petroleum jelly), paraffin (including liquid paraffin), or isoparaffins, or mixtures, thereof. In further embodiments, the hair coloring base compositions are free from at least petrolatum, petroleum jelly (including liquid petroleum jelly), paraffin (including liquid paraffin), isoparaffins, or mixtures, thereof.

(j) Cationic Conditioning Polymers

In various embodiments, the hair coloring base composition includes one or more cationic conditioning polymers. Nonlimiting examples include cationic polysaccharides derivatives, cationic gum derivatives, polymer derivatives of diallyldimethyl ammonium chloride, polymer derivatives of methacrylamidopropyltrimethylammonium chloride, cationic cellulose derivatives, quaternized hydroxyethyl cellulose, cationic starch derivatives, cationic guar gum derivatives (hydroxypropyl guar hydroxypropyltrimonium chloride), copolymers of acrylamide and dimethyldiallyammonium chloride, polyquaterniums, cocodimonium hydroxypropyl hydrolyzed rice protein, and a mixture thereof. A more exhaustive but nonlimiting list of cationic conditioning polymers is included later, under the heading "Cationic Conditioning Polymers."

The total amount of the one or more cationic conditioning polymers, if present, will vary. Nonetheless, in various embodiments, the total amount of the one or more cationic conditioning polymers in the hair coloring base composition is from about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. %, based on the total weight of the hair coloring base composition.

(k) Thickening Agents

In various embodiments, the hair coloring base composition includes one or more thickening agents. Nonlimiting examples of thickening agents include polyacrylate crosspolymers or crosslinked polyacrylate polymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. A more exhaustive but non-limiting list of thickening agents is included later, under the heading "Thickening Agents."

The total amount of the one or more thickening agents, if present, will vary. For example, in various embodiments, the hair coloring base composition includes one or more thickening agents in an amount of about 0.01 to about 10 wt. %, about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, based on the total weight of the hair coloring base composition.

(l) Silicones

The term "silicone" (or "silicones") refers to an "organosiloxane" and may be a silicone-based oil (or organosiloxane-based oil) containing silicone atoms, especially those having Si—O groups.

In various embodiments, the hair coloring base composition includes one or more silicones, preferably one or more silicone-based oils, one or more alkoxylated silicones, or a combination thereof.

The one or more silicones can be silicone-based oils that are volatile or non-volatile. Silicone-based oils include linear, branched, and cyclic silicone oils and include volatile and non-volatile silicone oils. Nonlimiting examples include polydimethylsiloxane (dimethicone), dimethiconol, amodimethicone, phenyl-modified silicone, silicone block copolymers containing amine groups or quat groups or other charged or uncharged silicone block copolymers, and blends of any of the foregoing. Additional nonlimiting examples include octamethylcyclotetrasiloxane, decamethylcyclopentasiloxane, dodecamethylcyclohexasiloxane, heptamethylhexyltrisiloxane, heptamethyl-octyltrisiloxane, hexamethyldisiloxane, octamethyltrisiloxane, decamethyltetrasiloxane and dodecamethylpentasiloxane, and mixtures thereof. In a preferred embodiment, the leave-on hair styling composition includes at least one silicone-based oil selected from dimethicone, dimethiconol, amodimethicone, and a combination thereof.

In various embodiments, the hair coloring base composition preferably includes one or more alkoxylated silicone. Nonlimiting examples of alkoxylated silicones include crosslinked organosiloxane emulsifiers such as dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer, and combinations thereof. In various embodiments, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone; PEG/PPG-4/12 dimethicone, and a combination thereof.

In a preferred embodiment, the hair coloring base composition includes one or more silicones selected from PEG/

PPG-4/12 dimethicone, PEG-10 dimethicone, PEG-12 dimethicone, PEG-14 dimethicone, PEG-17 dimethicone, PPG-12 dimethicone, PPG-17 dimethicone, and derivatized/functionalized forms thereof such as Bis-PEG/PPG-20/20 dimethicone bis-PEG/PPG-16/16 PEG/PPG-16/16 dimethicone, PEG/PPG-14/4 dimethicone, PEG/PPG-20/20 dimethicone, PEG/PPG-20/23 dimethicone, dimethicone, dimethiconol, amodimethicone, or a combination thereof.

In other preferred embodiments, the hair coloring base composition is free or essentially free from silicones (any silicone-containing compound). Nonetheless, in preferred embodiments, the hair coloring base composition is free or essentially free from silicone-based oils. In preferred embodiments, the hair coloring base composition is free or essentially free from alkoxylated silicones.

The total amount of the one or more silicones, if present, will vary but is typically from about 0.01 to about 10 wt. %, based on the total weight of the hair coloring compositions. In further embodiments, the hair coloring composition includes about 0.01 to about 8 wt. %, about 0.01 to about 5 wt. %, about 0.01 to about 3 wt. %, about 0.01 to about 1 wt. %, about 0.1 to about 10 wt. %, about 0.1 to about 8 wt. %, about 0.1 to about 5 wt. %, about 0.1 to about 3 wt. %, about 0.1 to about 1 wt. %, about 1 to about 10 wt. %, about 1 to about 8 wt. %, about 1 to about 5 wt. %, or about 1 to about 3 wt. % of the one or more silicones, based on the total weight of the hair coloring base composition. In a preferred embodiment, the hair coloring base composition includes about 0.01 to about 5 wt. %, preferably about 0.1 to about 4 wt. %, more preferably about 0.5 to about 3 of the one or more silicones.

(m) Non-Oxidative Dye Colorants

In addition to the oxidative dyes, the hair coloring composition may include one or more or additional non-oxidative dye colorants. The non-oxidative dye colorants can be any colorants appropriate for use on hair that is not an oxidative dye as discussed herein. For example, the colorant may be selected from direct dyes, pigments, natural colorants, and mixtures thereof. Other suitable hair colorants include, but are not limited to, liposoluble dyes, nacreous pigments, pearling agents, leuco dyes, optical lightening colorants, and optically-variable pigments. In some embodiments, the colorant includes at least one primary dye intermediate and/or a coupler compound.

Direct Dyes

A direct dye is a colored substance that does not require the use of an oxidizing agent in order to reveal its color. Suitable direct dyes that may be used in the hair coloring compositions may include or be chosen from acidic (anionic), basic (cationic), and neutral dyes. "Acidic dye" is generally intended to mean a dye containing at least one COOH, $SO_3H$, $PO_3H$, or $PO_4H_2$ group, it being possible for said groups to exist in the form of salts. "Salts" is generally intended to mean salts of metals (for example, alkali metals or alkaline earth metals), salts of an organic amine that may optionally be hydroxylated. Such dyes are also referred to as anionic dyes. Exemplary acidic dyes that may be suitably used in the hair coloring compositions include or can be chosen from acidic nitro dyes, acidic azo dyes, acidic azine dyes, acidic triarylmethane dyes, acidic quinone dyes, acidic indo-amine dyes and acidic natural dyes, and mixtures thereof.

"Basic dyes" is generally intended to mean a dye that has at least one group bearing a positive charge, such as an ammonium group or a quaternized nitrogen atom in a ring. Such dyes are also referred to as cationic dyes. Suitable basic dyes that may be used in hair coloring compositions include and/or can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Preferably, the direct dyes may be present in amounts ranging from 0.001% to 30% by weight, preferably from 0.01% to 20% by weight, or more preferably from 0.1% to 10% by weight, based on the total weight of the coloring composition.

Pigments

The hair coloring compositions, in some instances, may include pigments, such as those chosen from white, colored, inorganic, organic, polymeric, nonpolymeric, coated and uncoated pigments. Non-limiting examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, and mixtures thereof. Non-limiting examples of organic pigments include carbon black, pigments of D & C type, and lakes based on cochineal carmine, barium, strontium, calcium, and aluminum. Other examples of pigments include ultramarines, HC Blue No. 14, Ext. Yellow 7, Yellow 10 Lake, and acid violet 43.

If present, the pigments may be present in the hair coloring composition in a concentration ranging up to 50 wt. % of the total weight of the coloring composition, such as from 0.5 to 40 wt. % or from 2 to 30 wt. % based on the total weight of the coloring composition.

Natural Colorants

The hair coloring composition may include one or more natural colorants. Non-limiting examples of natural colorants include those disclosed in US patent application publication no. US 2003/0159221, the entire contents of which is hereby incorporated by reference. As used herein, the phrase "natural colorant" refers to compounds that exist in nature, whether they have been obtained by extraction or reproduced chemically. Examples of natural direct dyes that may be used in the hair coloring composition include and/or may be chosen from lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes and especially henna-based poultices or extracts.

If present, the natural colorants may be incorporated in the hair coloring composition in a concentration ranging up to 50 wt. % based on the total weight of the hair coloring composition, such as from 0.05 to 40 wt. % or from 2 to 30 wt. % based on the total weight of the hair coloring composition.

Liposoluble Dyes

Optionally, the hair coloring composition may include one or more liposoluble dyes. Examples of liposoluble dyes that may be used in the hair coloring compositions include and/or may be chosen from Sudan Red, DC Red 17, DC Green 6, β-carotene, soybean oil, Sudan Brown, DC Yellow 11, DC Violet 2, DC Orange 5, DC Blue No. 14, annatto, and quinoline yellow. The liposoluble dyes, when present, may have a concentration ranging up to 20 wt. % of the total weight of the hair coloring composition, such as from 0.0001 to 6 wt. % or 0.1 to 4 wt. % of the total weight of the hair coloring composition.

Nacreous Pigments

In some instances, the hair coloring composition includes one or more nacreous pigments. Exemplary nacreous pigments that may be used in the hair coloring compositions include and/or may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the coloring base composition in a concentration ranging up to 50% by weight of the total weight of the hair coloring composition, such as from 0.1% to 20% or preferably from 0.1% to 15% by weight of the total weight of the hair coloring composition.

Leuco Dyes

The hair coloring compositions may also include one or more Leuco dyes. Non-limiting examples of leuco dyes include those disclosed in US patent application publication no. 20040194231, the entire content of which is hereby incorporated by reference. Leuco dyes are usually only slightly colored or are not colored at all and can be converted by simple oxidation in air or in the presence of an oxidizing agent into a triheteroylmethane compound. Examples of leuco dyes and corresponding triheteroylmethane compounds that may be used in the hair coloring compositions include and/or may be chosen from 1H-Benzo[ij]quinolizinium, 9-[bis(2,3,6,7-tetrahydro-1H,5H-benzo[ij-]quinolizin-9-yl)methylene]-2,3,5,6,7,9-hexahydro-chloride; 5H-Benzo[a]carbazolium, 11-ethyl-5-[(11-ethyl-11H-benzo[a]carbazol-5-yl)(1-ethyl-1,2,3,4-tetrahydro-5-quinolinyl)methylene]-; Pyrrolo[3,2,1-ij]quinolinium, 8-[bis(1,2,5,6-tetrahydro-4H-pyrrolo[-3,2,1-ij]quinolin-8-yl)methylene]-1,2,4,5,6,8-hexahydro-; Tri(9-ethy-9H-carbazol-3-yl)methane; bis(6-Chloro-9-ethy-9H-carbazol-3-yl)-(9-ethy-9H-carbazol-3-yl)methane; bis(1-(4-sulfo-butyl)-2,3,4,6-tetrahydro-quinolinium)-pyrid-4-yl-methane; bis(1-ethyl-2-methyl-1H-indol-3-yl)-(9-ethy-9H-carbazol-3-yl)methane; Tri(7-ethyl-7H-benzo[c]carbazol-10-yl)methane; bis((6-dimethylamino-3-methyl-1H-indol-2-yl)-2-furylmethane; bis((6-dimethylamino-3-methyl-1H-indol-2-yl)-(pyrid-4-yl)methane; bis(1-ethyl-2-methyl-1H-indol-3-yl)-2-thienylmethane; 3-[(1-ethyl-2-methyl-1H-indol-3-yl)-(9-ethy-9H-carbazol-3-yl) methylene]-1-ethyl-2-methyl-3H-indolium; 3-[(1-ethyl-2-methyl-1H-indol-3-yl)-2-thienyl)methylene]-1-ethyl-2-methyl-3H-indolium; and combinations thereof.

Optical Lightening Colorants

Examples of optical lightening colorants include those disclosed in US patent application publication no. US20040205905, the entire content of which is hereby incorporated by reference.

The total amount of the one or more non-oxidative dye colorants, if present, will vary. Nonetheless, in certain embodiments the total amount of the one or more non-oxidative dye colorants, if present, is from about 0.01 to about 5 wt. %, about 0.01 to about 3 wt. %, about 0.01 to about 2 wt. %, about 0.1 to about 5 wt. %, about 0.1 to about 3 wt. %, about 0.1 to about 2 wt. %, or about 0.1 to about 1 wt. %, based on the total weight of the hair coloring base composition.

Non-Cationic Conditioning Agents

The hair coloring base composition may optionally include one or more non-cationic conditioning agents. For example, the hair coloring base compositions may optionally include one or more glyceryl ethers as conditioning agent(s). Non-limiting examples of glyceryl ethers include glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Particularly useful glyceryl ethers also include glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, and a mixture thereof. In some instances, glyceryl lauryl ether is particularly useful.

The total amount of the one or more non-cationic conditioning agents, if present, may vary but is typically about 0.1 to about 15 wt. %, based on the total weight of the hair coloring base composition. The total amount of the one or more miscellaneous conditioning agents can be about 0.1 to about 10 wt. %, 0.1 to about 5 wt. %, about 0.5 to about 15 wt. %, about 0.5 to about 10 wt. %, about 0.5 to about 5 wt. %, or about 1 to about 10 wt. %, or about 1 to about 5 wt. %, based on the total weight of the hair coloring base composition.

Miscellaneous Ingredients

The hair coloring compositions of the instant disclosure (hair coloring base compositions, developer compositions, and/or the ready-to-use hair coloring compositions) may optionally include (or optionally exclude) one more miscellaneous ingredients. Miscellaneous ingredients are ingredients that are compatible with the hair coloring base composition and the ready-to-use hair coloring composition but do not disrupt or materially affect the basic and novel properties of the compositions. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, amino acids, carboxylic acids, fillers, composition colorants, etc. In various embodiments, the miscellaneous ingredients are chosen from preservatives, fragrances, pH adjusters, salts, chelating agents, buffers, composition colorants, amino acids, carboxylic acids, peptides, botanical extracts, and mixtures thereof. In the context of the instant disclosure, a "composition colorant" is a compound that colors the composition but does not have an appreciable coloring effect on hair. In other words, the composition colorant is included to provide a coloring to the composition for aesthetic appeal, which is not intended to impart coloring properties to hair. Styling gels, for example, can be found in a variety of different colors (e.g., light blue, light pink, etc.) yet application of the styling gel to the hair does not change the color of the hair.

Amino Acids

In various embodiments, at least one of the one or more miscellaneous ingredients is an amino acid. As used herein, the term "amino acid" includes amino acids such as proteinogenic amino acids, amino sulfonic acids, and salts thereof. Amino acids are simple organic compounds containing both a carboxylic acid group (—COOH) and an amino group (—NH$_2$). Amino sulfonic acids are simple organic compounds containing both a sulfonic acid group (—SO$_2$OH) and an amino group (—NH$_2$). Well-known amino acids include the twenty amino acids that form the proteins of living organisms (standard proteinogenic amino acids): alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. The amino acids of the instant disclosure, however, are not limited to the standard proteinogenic amino acids.

Non-limiting examples of amino sulfonic acids include aminomethane sulfonic acid, 2-aminoethane sulfonic acid (taurine), aminopropane sulfonic acid, aminobutane sulfonic acid, aminohexane sulfonic acid, aminoisopropyl sulfonic acid, aminododecyl sulfonic acid, aminobenzene sulfonic acid, aminotoulene sulfonic acid, sulfanilic acid, chlorosulfanilic acid, diamino benzene sulfonic acid, amino phenol sulfonic acid, amino propyl benzene sulfonic acid, amino hexyl benzene sulfonic acid, and a mixture thereof.

In various embodiments, charged amino acids may be used. Nonlimiting examples of charged amino acids include arginine, lysine, aspartic acid, and glutamic acid. In some cases, polar amino acids are useful. Non-limiting examples of polar amino acids include glutamine, asparagine, histidine, serine, threonine, tyrosine, cysteine, methionine, and tryptophan.

In various embodiments, hydrophobic amino acids may be employed. Nonlimiting examples of hydrophobic amino acids include alanine, isoleucine, leucine, phenylalanine, valine, proline, and glycine.

In certain exemplary embodiments, the hair coloring base composition includes at least one amino acid selected from glycine, alanine, serine, beta-alanine, taurine, sodium glycinate, sodium alaninate, sodium serinate, lithium beta-alanine, sodium taurate, or combinations thereof. In further exemplary embodiments, one or more amino acids is included in the hair coloring base composition selected from aspartic acid, cysteine, glycine, lysine, methionine, proline, tyrosine, phenylalanine, carnitine, taurine, or a salt thereof. In another exemplary embodiment, the hair coloring base composition includes wheat amino acids.

In a preferred embodiment, the hair coloring base composition includes an amino acid selected from taurine, glycine, wheat amino acids, or a combination thereof. In a preferred exemplary embodiment, the hair coloring base composition includes at least taurine. In another preferred exemplary embodiment, the hair coloring base composition includes wheat amino acids, taurine, or a combination thereof.

The total amount of the one or more amino acids, if present, will vary but is typically from about 0.01 to about 10 wt. %, based on the total weight of the hair coloring base composition. In further embodiments, the total amount of the one or more amino acids in the hair coloring base composition is about 0.01 to about 5 wt. %, about 0.01 to about 3 wt. %, about 0.01 to about 1 wt. %, about 0.05 to about 10 wt. %, about 0.05 to about 5 wt. %, about 0.05 to about 3 wt. %, about 0.05 to about 1 wt. %, about 0.1 to about 10 wt. %, about 0.1 to about 5 wt. %, about 0.1 to about 3 wt. %, about 0.1 to about 2 wt. %, or about 0.1 to about 1 wt. %, based on the total weight of the hair coloring base composition. Preferably, the hair coloring base composition includes about 0.01 to about 5 wt. %, more preferably about 0.05 to about 4 wt. %, and even more preferably about 0.1 to about 2 wt. % of the one amino acids.

Carboxylic Acids

In various embodiments, at least one of the one or more miscellaneous ingredients is a carboxylic acid. As used herein, the term "carboxylic acid" includes salts of carboxylic acids. In certain embodiments, the carboxylic acids include non-polymeric mono, di, and/or tricarboxylic acid which are organic compounds having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of mono-carboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair coloring base compositions include at least lactic acid and/or a salt thereof.

Non-limiting examples of di-carboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair coloring base compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair coloring base compositions include at least citric acid and/or a salt thereof.

In one or more embodiments, the hair coloring base composition comprises at least one carboxylic acid selected from oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof. In a preferred embodiment, the hair coloring base composition includes erythrobic acid, citric acid, or a combination thereof.

The total amount of one or more carboxylic acids in the hair coloring base composition will vary but is typically in the range from about 0.01 to about 10 wt. % based on the total weight of the hair coloring base composition. In further embodiments, the total amount of the one or more carboxylic acids in the hair coloring base composition is about 0.01 to about 5 wt. %, about 0.01 to about 3 wt. %, about 0.01 to about 1 wt. %, about 0.05 to about 10 wt. %, about 0.05 to about 5 wt. %, about 0.05 to about 3 wt. %, about 0.05 to about 1 wt. %, about 0.1 to about 10 wt. %, about 0.1 to about 5 wt. %, about 0.1 to about 3 wt. %, about 0.1 to about 2 wt. %, or about 0.1 to about 1 wt. %, based on the total weight of the hair coloring base composition. Preferably, the hair coloring base composition includes about 0.01 to about 5 wt. %, more preferably about 0.05 to about 4 wt. %, and even more preferably about 0.1 to about 2 wt. % of the one or more carboxylic acids.

The total amount of the one or more miscellaneous ingredients, if present, will vary. Nonetheless, in various embodiments, the compositions of the instant disclosure (hair coloring base compositions, developer compositions, and/or the ready-to-use hair coloring compositions) include, if present, from about 0.001 to about 10 wt. % of one or more miscellaneous ingredients. In further embodiments, the compositions of the instant disclosure include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients.

PREFERRED EMBODIMENTS

In a preferred embodiment, the hair coloring base composition comprises, consists essentially of, or consists of:
(a) about 0.01 to about 5 wt. %, preferably about 0.05 to about 3 wt. %, more preferably about 0.1 to about 1 wt. % of 2-methoxymethyl-P-phenylenediamine, and optionally one or more additional oxidative dye precursors, wherein component (a) preferably comprises:
  (a)(i) about 0.01 to about 5 wt. %, preferably about 0.05 to about 3 wt. %, more preferably about 0.1 to about 1 wt. % of 2-methoxymethyl-P-phenylenediamine;
  (a)(ii) optionally, about 0.001 to about 5 wt. %, preferably about 0.01 to about 3 wt. %, more preferably about 0.1 to about 1 wt. % of one or more additional oxidative dye precursors, wherein the one or more additional oxidative dye precursors are preferably selected from para-phenylenediamines, bis(phenyl) alkylenediamines, para-aminophenols, ortho-aminophenols and heterocyclic bases, and the addition salts thereof, more preferably wherein the additional oxidative dye precursors are selected from dimethylpiperazinium aminopyrazolopyridine, 2,3-diaminodihydropyrazolo pyrazolone dimethosulfonate, salts thereof, and combinations thereof;
(b) about 0.001 to about 5 wt. %, preferably about 0.01 to about 4 wt. %, more preferably about 0.1 to about 3 wt. % of one or more couplers, wherein the one or more couplers are preferably selected from meta-aminophenols, meta-phenylenediamines and meta-diphenols, naphthols, mono- or polyhydroxylated naphthalene derivatives, heterocyclic couplers, or combinations thereof, more preferably wherein at least one of the couplers is selected from 2-amino-3-hydroxypyridine, hydroxybenzomorpholine, 2-methyl-5-hydroxyethyl-aminophenol, 2-methylrescorcinol, 2,4-diaminophenoxy-ethanol HCL, 5-amino-6-chloro-o-cresol, 1-naphthol, or a combination thereof;
(c) 3 wt. % or less, preferably 2.5 wt. % or less, more preferably 2 wt. % or less, even more preferably 1.5 wt. % or less of one or more alkalizing agents, wherein the one or more alkalizing agents is preferably selected from alkanolamines, preferably wherein the one or more alkanolamines are selected from monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, or a mixture thereof, most preferably wherein the alkanolamine is monoethanolamine;
(d) optionally, about 0.1 to about 15 wt. %, preferably about 1 to about 12 wt. %, more preferably about 1 to about 10 wt. % of one or more fatty alcohols having from 12 to 24 carbon atoms, preferably chosen from cetyl alcohol, stearyl alcohol, cetearyl alcohol, behenyl alcohol, lauryl alcohol, myristic or myristyl alcohol, arachidyl alcohol, lignoceryl alcohol, oleyl alcohol, or combinations thereof;
(e) about 10 to about 40 wt. %, preferably about 15 to about 35 wt. %, more preferably about 20 to about 30 wt. % of one or more surfactants, wherein preferably at least one of the one or more surfactants is a nonionic surfactant, more preferably wherein the hair coloring base composition comprises:
  (e)(1) about 5 to about 35 wt. %, preferably about 10 to about 25 wt. %, even more preferably about 14 to about 28 wt. % of one or more nonionic surfactants; and
  (e)(2) about 0.1 to about 15 wt. %, preferably about 1 to about 12 wt. %, more preferably about 2 to about 12 wt. % of one or more anionic surfactants, preferably one or more non-sulfate-based anionic surfactants;
(f) about 1 to about 40 wt. %, preferably about 1 to about 30 wt. %, more preferably about 2 to about 25 wt. % of one or more water-soluble organic solvents, in particular, one or more water-soluble organic solvents chosen from glycerin, mono-alcohols, polyols (polyhydric alcohols), glycols, and a mixture thereof, preferably, the one or more water-soluble solvents are chosen from glycerin, propylene glycol, butylene glycol, pentylene glycol, dipropylene glycol, hexylene glycol, ethanol, isopropanol, t-butyl alcohol, PPG-2 butyl ether, or mixtures thereof;
(g) about 25 to about 80 wt. %, preferably about 30 to about 75 wt. %, more preferably about 40 to about 75 wt. % of water;
  wherein (e), (f), and (g) are in amounts such that a combined amount of (e), (f), and (g) constitutes at least 70 wt. %, preferably at least 75 wt. %, more preferably at least 80 wt. %, and even more preferably at least 85 wt. % of the hair coloring base composition;
(h) optionally, about 0.1 to about 10 wt %, preferably about 0.1 to about 5 wt. %, more preferably about 0.1 to about 3 wt. % of one or more reducing agents, for example, chosen from potassium metabisulfite, potassium sulfite, sodium hydrosulfite, sodium metabisulfite, sodium sulfite, sodium bisulphite, thioglycolic acid, thiolactic acid, ammonium thiolactate, dehydroascorbic acid, a salt thereof, and a mixture thereof, preferably thioglycolic acid, thiolatic acid, salts thereof (e.g., ammonium thiolactate), sodium sulfite, or mixtures thereof; and
(i) optionally, about 0.01 to about 10 wt. %, preferably about 0.05 to about 8 wt. %, more preferably about 0.1 to about 5 wt. % of one or more fatty compounds other than the fatty alcohols of (d), preferably wherein at least one of the one or more fatty compounds is an oil, preferably a natural oil from a plant;
(j) optionally, about 0.01 to about 10 wt. %, preferably about 0.1 to 8 wt. %, more preferably about 0.1 to about 5 wt. % of one or more miscellaneous ingredients, for example, preservatives, fragrances, pH adjusters, salts, chelating agents, buffers, antioxidants, flavonoids, vitamins, botanical extracts, UV filtering agents, proteins, protein hydrolysates, and/or isolates, amino acids, carboxylic acids, fillers, composition colorants, and mixtures thereof, preferably wherein:
  at least one of the one or more miscellaneous ingredients is an amino acid in an amount of about 0.01 to about 8 wt. %, preferably about 0.1 to about 5 wt. %, more preferably about 0.1 to about 2 wt. %, wherein preferably the amino acid is selected from taurine, glycine, wheat amino acids, or a combination thereof;
  at least one of the one or more miscellaneous ingredients is a carboxylic acid in an amount of 0.01 to about 8 wt. %, preferably about 0.05 to about 5 wt.

%, more preferably about 0.05 to about 2 wt. %, wherein the carboxylic acids are preferably selected from non-polymeric mono, di, and tricarboxylic acids, and/or salts thereof, typically having a molecular weight of less than about 500 g/mol, less than about 400 g/mol, or less than about 300 g/mol, wherein the carboxylic acids are preferably selected from erythorbic acid, oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof;
- (k) optionally, one or more thickening polymers;
- (l) optionally, one or more silicones;
- (m) optionally, one or more non-oxidative dye colorants; all percentages by weight are based on the total weight of the hair coloring base composition.

In another preferred embodiment, the hair coloring base composition comprises, consists essentially of, or consists of:
- (a) about 0.01 to about 5 wt. %, preferably about 0.05 to about 3 wt. %, more preferably about 0.1 to about 1 wt. % of 2-methoxymethyl-P-phenylenediamine, and optionally one or more additional oxidative dye precursors, wherein component (a) preferably comprises:
  - (a)(i) about 0.01 to about 5 wt. %, preferably about 0.05 to about 3 wt. %, more preferably about 0.1 to about 1 wt. % of 2-methoxymethyl-P-phenylenediamine;
  - (a)(ii) optionally, about 0.001 to about 5 wt. %, preferably about 0.01 to about 3 wt. %, more preferably about 0.1 to about 1 wt. % of one or more additional oxidative dye precursors, wherein the one or more additional oxidative dye precursors are preferably selected from para-phenylenediamines, bis(phenyl) alkylenediamines, para-aminophenols, ortho-aminophenols and heterocyclic bases, and the addition salts thereof, more preferably wherein the additional oxidative dye precursors are selected from dimethylpiperazinium aminopyrazolopyridine, 2,3-diaminodihydropyrazolo pyrazolone dimethosulfonate, salts thereof, and combinations thereof;
- (b) about 0.001 to about 5 wt. %, preferably about 0.01 to about 4 wt. %, more preferably about 0.1 to about 3 wt. % of one or more couplers, wherein the one or more couplers are preferably selected from meta-aminophenols, meta-phenylenediamines and meta-diphenols, naphthols, mono- or polyhydroxylated naphthalene derivatives, heterocyclic couplers, or combinations thereof, more preferably wherein at least one of the couplers is selected from 2-amino-3-hydroxypyridine, hydroxybenzomorpholine, 2-methyl-5-hydroxyethylaminophenol, 2-methylrescorcinol, 2,4-diaminophenoxy-ethanol HCL, 5-amino-6-chloro-o-cresol, 1-naphthol, or a combination thereof;
- (c) 3 wt. % or less, preferably 2.5 wt. % or less, more preferably 2 wt. % or less, even more preferably 1.5 wt. % or less of one or more alkalizing agents, wherein the one or more alkalizing agents is preferably selected from alkanolamines, preferably wherein the one or more alkanolamines are selected from monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, or a mixture thereof, most preferably wherein the alkanolamine is monoethanolamine;
- (d) optionally, about 0.1 to about 15 wt. %, preferably about 2 to about 15 wt. %, more preferably about 5 to about 12 wt. % of one or more fatty alcohols having from 12 to 24 carbon atoms, preferably chosen from cetyl alcohol, stearyl alcohol, cetearyl alcohol, behenyl alcohol, lauryl alcohol, myristic or myristyl alcohol, arachidyl alcohol, lignoceryl alcohol, oleyl alcohol, or combinations thereof;
- (e) about 10 to about 40 wt. %, preferably about 15 to about 35 wt. %, more preferably about 20 to about 30 wt. % of one or more surfactants, wherein preferably at least one of the one or more surfactants is a nonionic surfactant, more preferably wherein the hair coloring base composition comprises:
  - (e)(1) about 5 to about 35 wt. %, preferably about 10 to about 25 wt. %, even more preferably about 14 to about 28 wt. % of one or more nonionic surfactants; and
  - (e)(2) about 0.1 to about 15 wt. %, preferably about 1 to about 12 wt. %, more preferably about 2 to about 12 wt. % of one or more anionic surfactants, preferably one or more non-sulfate-based anionic surfactants;
  - (e)(3) about 0.01 to about 10 wt. %, preferably about 0.1 to about 5 wt. %, more preferably about 1 to about 5 wt. % of one or more amphoteric surfactants, wherein the one or more amphoteric surfactants are preferably selected from alkyl amphoproprionates, betaines, alkyl sultaines, alkyl amphoacetates, alkyl amphodiacetates, or a combination thereof, more preferably wherein at least one of the one or more amphoteric surfactants is a betaine selected from coco betaine, cocamidopropyl betaine, behenyl betaine, capryl/capramidopropyl betaine, and lauryl betaine, wherein particularly preferred betaines include coco-betaine, cocamidopropyl betaine, or a combination thereof;
- (f) about 10 to about 40 wt. %, preferably about 15 to about 35 wt. %, more preferably about 20 to about 30 wt. % of one or more water-soluble organic solvents, in particular, one or more water-soluble organic solvents chosen from glycerin, mono-alcohols, polyols (polyhydric alcohols), glycols, and a mixture thereof, preferably, the one or more water-soluble solvents are chosen from glycerin, propylene glycol, butylene glycol, pentylene glycol, dipropylene glycol, hexylene glycol, ethanol, isopropanol, t-butyl alcohol, PPG-2 butyl ether, or mixtures thereof;
- (g) about 25 to about 80 wt. %, preferably about 30 to about 70 wt. %, more preferably about 35 to about 60 wt. % of water;
  wherein (e), (f), and (g) are in amounts such that a combined amount of (e), (f), and (g) constitutes at least 70 wt. %, preferably at least 75 wt. %, more preferably at least 80 wt. %, and even more preferably at least 85 wt. % of the hair coloring base composition;
- (h) optionally, about 0.1 to about 10 wt %, preferably about 0.1 to about 5 wt. %, more preferably about 0.1 to about 3 wt. % of one or more reducing agents, for example, chosen from potassium metabisulfite, potassium sulfite, sodium hydrosulfite, sodium metabisulfite, sodium sulfite, sodium bisulphite, thioglycolic acid, thiolactic acid, ammonium thiolactate, dehydroascorbic acid, a salt thereof, and a mixture thereof, preferably thioglycolic acid, thiolatic acid, salts thereof (e.g., ammonium thiolactate), sodium sulfite, or mixtures thereof; and
(i) optionally, about 0.01 to about 15 wt. %, preferably about 0.05 to about 10 wt. %, more preferably about 1 to about 5 wt. % of one or more fatty compounds other than the fatty alcohols of (d), preferably wherein at least one of the one or more fatty compounds is an oil, preferably a natural oil from a plant;
(j) optionally, about 0.01 to about 10 wt. %, preferably about 0.01 to 5 wt. %, more preferably about 0.1 to about 5 wt. % of one or more miscellaneous ingredients, for example, preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, cationic polymers, thickening agents, and mixtures thereof, preferably wherein:
at least one of the one or more miscellaneous ingredients is an amino acid in an amount of about 0.01 to about 8 wt. %, preferably about 0.1 to about 5 wt. %, more preferably about 0.1 to about 2 wt. %, wherein preferably the amino acid is selected from taurine, glycine, wheat amino acids, or a combination thereof;
at least one of the one or more miscellaneous ingredients is a carboxylic acid in an amount of 0.01 to about 8 wt. %, preferably about 0.05 to about 5 wt. %, more preferably about 0.05 to about 2 wt. %, wherein the carboxylic acids are preferably selected from non-polymeric mono, di, and tricarboxylic acids, and/or salts thereof, typically having a molecular weight of less than about 500 g/mol, less than about 400 g/mol, or less than about 300 g/mol, wherein the carboxylic acids are preferably selected from erythorbic acid, oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof;
(k) optionally, one or more thickening polymers;
(l) optionally, one or more silicones;
(m) optionally, one or more non-oxidative dye colorants;
all percentages by weight are based on the total weight of the hair coloring base composition.

In yet another embodiment, the hair coloring base composition comprises, consists essentially of, or consists of:
(a) about 0.01 to about 5 wt. %, preferably about 0.05 to about 3 wt. %, more preferably about 0.1 to about 1 wt. % of 2-methoxymethyl-P-phenylenediamine, and optionally one or more additional oxidative dye precursors, wherein component (a) preferably comprises:
(a)(i) about 0.01 to about 5 wt. %, preferably about 0.05 to about 3 wt. %, more preferably about 0.1 to about 1 wt. % of 2-methoxymethyl-P-phenylenediamine;
(a)(ii) optionally, about 0.001 to about 5 wt. %, preferably about 0.01 to about 3 wt. %, more preferably about 0.1 to about 1 wt. % of one or more additional oxidative dye precursors, wherein the one or more additional oxidative dye precursors are preferably selected from para-phenylenediamines, bis(phenyl) alkylenediamines, para-aminophenols, ortho-aminophenols and heterocyclic bases, and the addition salts thereof, more preferably wherein the additional oxidative dye precursors are selected from dimethylpiperazinium aminopyrazolopyridine, 2,3-diaminodihydropyrazolo pyrazolone dimethosulfonate, salts thereof, and combinations thereof;
(b) about 0.001 to about 5 wt. %, preferably about 0.01 to about 4 wt. %, more preferably about 0.1 to about 3 wt. % of one or more couplers, wherein the one or more couplers are preferably selected from meta-aminophenols, meta-phenylenediamines and meta-diphenols, naphthols, mono- or polyhydroxylated naphthalene derivatives, heterocyclic couplers, or combinations thereof, more preferably wherein at least one of the couplers is selected from 2-amino-3-hydroxypyridine, hydroxybenzomorpholine, 2-methyl-5-hydroxyethyl-aminophenol, 2-methylrescorcinol, 2,4-diaminophenoxy-ethanol HCL, 5-amino-6-chloro-o-cresol, 1-naphthol, or a combination thereof;
(c) 3 wt. % or less, preferably 2.5 wt. % or less, more preferably 2 wt. % or less, even more preferably 1.5 wt. % or less of one or more alkalizing agents, wherein the one or more alkalizing agents is preferably selected from alkanolamines, preferably wherein the one or more alkanolamines are selected from monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, or a mixture thereof, most preferably wherein the alkanolamine is monoethanolamine;
(d) optionally, less than 12 wt. %, preferably less than 5, more preferably less than 1 wt. %, even more preferably less than 0.1 wt. % of one or more fatty alcohols having from 12 to 24 carbon atoms, wherein the hair coloring base composition may be free or essentially free from fatty alcohols;
(e) about 10 to about 40 wt. %, preferably about 15 to about 35 wt. %, more preferably about 20 to about 30 wt. % of one or more surfactants, wherein preferably at least one of the one or more surfactants is a nonionic surfactant, more preferably wherein the hair coloring base composition comprises:
(e)(1) about 5 to about 35 wt. %, preferably about 10 to about 25 wt. %, even more preferably about 14 to about 28 wt. % of one or more nonionic surfactants; and
(e)(2) about 0.1 to about 15 wt. %, preferably about 1 to about 12 wt. %, more preferably about 2 to about 12 wt. % of one or more anionic surfactants, preferably one or more non-sulfate-based anionic surfactants;
(f) optionally, about 0.1 to about 15 wt. %, preferably about 1 to about 10 wt. %, more preferably about 2 to about 8 wt. % of one or more water-soluble organic solvents, in particular, one or more water-soluble organic solvents chosen from glycerin, mono-alcohols, polyols (polyhydric alcohols), glycols, and a mixture thereof, preferably, the one or more water-soluble solvents are chosen from glycerin, propylene glycol, butylene glycol, pentylene glycol, dipropylene glycol, hexylene glycol, ethanol, isopropanol, t-butyl alcohol, PPG-2 butyl ether, or mixtures thereof;
(g) about 50 to about 80 wt. %, preferably about 60 to about 75 wt. %, more preferably about 60 to about 75 wt. % of water;
wherein (e), (f), and (g) are in amounts such that a combined amount of (e), (f), and (g) constitutes at least 70 wt. %, preferably at least 75 wt. %, more preferably at least 80 wt. %, and even more preferably at least 85 wt. % of the hair coloring base composition;
(h) optionally, about 0.1 to about 10 wt %, preferably about 0.1 to about 5 wt. %, more preferably about 0.1 to about 3 wt. % of one or more reducing agents, for example, chosen from potassium metabisulfite, potassium sulfite, sodium hydrosulfite, sodium metabisulfite, sodium sulfite, sodium bisulphite, thioglycolic acid, thiolactic acid, ammonium thiolactate, dehydroascorbic acid, a salt thereof, and a mixture thereof, preferably thioglycolic acid, thiolatic acid, salts thereof (e.g., ammonium thiolactate), sodium sulfite, or mixtures thereof; and
(i) optionally, about 0.01 to about 10 wt. %, preferably about 0.05 to about 8 wt. %, more preferably about 0.1 to about 5 wt. % of one or more fatty compounds other than the fatty alcohols of (d), preferably wherein at least one of the one or more fatty compounds is an oil, preferably a natural oil from a plant;
(j) optionally, about 0.01 to about 10 wt. %, preferably about 0.01 to 5 wt. %, more preferably about 0.1 to about 5 wt. % of one or more miscellaneous ingredients, for example, preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, and mixtures thereof, preferably wherein:
at least one of the one or more miscellaneous ingredients is an amino acid in an amount of about 0.01 to about 8 wt. %, preferably about 0.1 to about 5 wt. %, more preferably about 0.1 to about 2 wt. %, wherein preferably the amino acid is selected from taurine, glycine, wheat amino acids, or a combination thereof;
at least one of the one or more miscellaneous ingredients is a carboxylic acid in an amount of 0.01 to about 8 wt. %, preferably about 0.05 to about 5 wt. %, more preferably about 0.05 to about 2 wt. %, wherein the carboxylic acids are preferably selected from non-polymeric mono, di, and tricarboxylic acids, and/or salts thereof, typically having a molecular weight of less than about 500 g/mol, less than about 400 g/mol, or less than about 300 g/mol, wherein the carboxylic acids are preferably selected from erythorbic acid, oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof;
(k) optionally, one or more thickening polymers;
(l) optionally, one or more silicones;
(m) optionally, one or more non-oxidative dye colorants;
all percentages by weight are based on the total weight of the hair coloring base composition.

Furthermore, the total amount of alkalizing agent (e.g., monoethanolamine) in the hair coloring base composition such that when mixed with a developer composition to form a ready-to-use hair coloring composition, the total amount of alkalizing agent in the ready-to-use coloring composition is less than 2 wt. %, preferably less than 1.5 wt. %, more preferably less than 1 wt. %

For example, the hair coloring base compositions are such that they form a ready-to-use hair coloring composition having the pH values described herein upon mixing with a developer composition comprising hydrogen peroxide in a weight ratio about 1:1 (hair coloring composition: developer composition), wherein the developer composition consists of:
(a) about 7.5 wt. % hydrogen peroxide;
(b) about 82 wt. % water;
(c) about 0.5 wt. % glycerin;
(d) about 2.3 wt. % of cetearyl alcohol;
(e) about 0.9 wt. % of trideceth-2 carboxamide MEA;
(f) about 0.6 wt. % ceteareth-25; and
wherein all percentages by weight for components of the developer composition are based on the total weight of the developer composition.

The developer composition described above is non-limiting and is provided simply as an example or standard to determine whether a hair coloring base composition results in a ready-to-use coloring composition having the claimed pH when mixed at the specified ratio

EXAMPLES

Implementation of the present disclosure is provided by way of the following examples. The examples serve to illustrate the technology without being limiting in nature.

Example 1

Inventive Formulas 1-7

|   |   |   | F1 | F2 | F3 | F4 | F5 | F6 | F7 |
|---|---|---|---|---|---|---|---|---|---|
| a) | BASE DYE | 2-METHOXYMETHYL-P-PHENYLENEDIAMINE | 0.4 | 0.4 | 0.4 | 0.4 | 0.4 | 0.4 | 0.4 |
| b) | COUPLER | 2-METHYL-5-HYDROXYETHYLAMINOPHENOL | 0.4 | | | | | | |
|   |   | 2,4-DIAMINOPHENOXYETHANOL HCl | | | | 0.6 | | | |
|   |   | 4-AMINO-2-HYDROXYTOLUENE | | | 0.3 | | | | |
|   |   | 2-AMINO-3-HYDROXYPYRIDINE | | | | | | 0.3 | |
|   |   | m-AMINOPHENOL | | | | | | | 0.3 |
|   |   | 5-AMINO-6-CHLORO-o-CRESOL | | 0.4 | | | | | |
|   |   | 1-NAPHTHOL | | | | | 0.4 | | |
| c) | ALKALIZING A. | ETHANOLAMINE | 0.4 | 0.4 | 0.4 | 0.4 | 0.4 | 0.4 | 0.4 |
| d) | FATTY ALCOHOL | OLEYL ALCOHOL | 6.0 | 6.0 | 6.0 | 6.0 | 6.0 | 6.0 | 6.0 |
| e) | SURFACTANTS | COCO-BETAINE, PPG-5-CETETH-10 PHOSPHATE, DECETH-3, LAURYL ALCOHOL, COCAMIDE MIPA, SODIUM C14-16 OLEFIN SULFONATE | 44 | 44 | 44 | 44 | 44 | 44 | 44 |

-continued

|   |   |   | F1 | F2 | F3 | F4 | F5 | F6 | F7 |
|---|---|---|---|---|---|---|---|---|---|
| f) | WS SOLVENTS | ALCOHOL DENAT, PROPYLENE GLYCOL, PPG-2 BUTYL ETHER, | 22 | 22 | 22 | 22 | 22 | 22 | 22 |
| g) | WATER | WATER | q.s. | q.s. | q.s. | q.s. | q.s. | q.s. | q.s. |
| h) | REDUCING A. | SODIUM SULFITE | 0.5 | 0.5 | 0.5 | 0.5 | 0.5 | 0.5 | 0.5 |
|   | SILICON | PEG/PPG-4/12 DIMETHICONE | 1.5 | 1.5 | 1.5 | 1.5 | 1.5 | 1.5 | 1.5 |
|   | MISC. |   | ≤5 | ≤5 | ≤5 | ≤5 | ≤5 | ≤5 | ≤5 |

* The composition "F1," "F2," "F3," "F4," "F5," "F6," and "F7," are abbreviations for Formula 1, Formula 2, Formula 3, Formula 4, Formula 5, Formula 6, and Formula 7, which are also abbreviated as "Fla 1," "Fla 2," "Fla 3," "Fla 4," "Fla 5," "Fla 6," and "Fla 7."

Example 2

Comparative Formulas (a)-(f)

|   |   |   | F(a) | F(b) | F(c) | F(d) | F(e) | F(f) |
|---|---|---|---|---|---|---|---|---|
| a) | BASE DYE | TOLUENE-2,5-DIAMINE (and) THIOGLYCERIN | 0.3 | 0.3 | 0.3 | 0.3 | 0.3 | 0.3 |
| b) | COUPLER | 2-METHYL-5-HYDROXYETHYLAMINOPHENOL | 0.4 |   |   |   |   |   |
|   |   | 2,4-DIAMINOPHENOXYETHANOL HCl |   |   |   | 0.6 |   |   |
|   |   | 4-AMINO-2-HYDROXYTOLUENE |   |   | 0.3 |   |   |   |
|   |   | 2-AMINO-3-HYDROXYPYRIDINE |   |   |   |   | 0.3 |   |
|   |   | m-AMINOPHENOL |   |   |   |   |   | 0.3 |
|   |   | 5-AMINO-6-CHLORO-o-CRESOL |   | 0.4 |   |   |   |   |
| c) | ALKALIZING A | ETHANOLAMINE | 0.4 | 0.4 | 0.4 | 0.4 | 0.4 | 0.4 |
| d) | FATTY ALCOHOL | OLEYL ALCOHOL | 6.0 | 6.0 | 6.0 | 6.0 | 6.0 | 6.0 |
| e) | SURFACTANTS | COCO-BETAINE, PPG-5-CETETH-10 PHOSPHATE, DECETH-3, LAURYL ALCOHOL, COCAMIDE MIPA, SODIUM C14-16 OLEFIN SULFONATE | 44 | 44 | 44 | 44 | 44 | 44 |
| f) | WS Solvents | ALCOHOL DENAT, PROPYLENE GLYCOL, PPG-2 BUTYL ETHER | 22 | 22 | 22 | 22 | 22 | 22 |
| g) | WATER | WATER | q.s. | q.s. | q.s. | q.s. | q.s. | q.s. |
| h) | REDUCING A. | SODIUM SULFITE | 0.5 | 0.5 | 0.5 | 0.5 | 0.5 | 0.5 |
|   | SILICON | PEG/PPG-4/12 DIMETHICONE | 1.5 | 1.5 | 1.5 | 1.5 | 1.5 | 1.5 |
|   | MISC. |   | ≤5 | ≤5 | ≤5 | ≤5 | ≤5 | ≤5 |

* The composition "F(a)," "F(b)," "F(c)," "F(d)," "F(e)," and "F(f)," are abbreviations for Formula (a), Formula (b), Formula (c), Formula (d), Formula (e), and Formula (f), which are also abbreviated as "Fla a," "Fla b," "Fla c," "Fla d," "Fla e," and "Fla f."

Example 3

Developer Composition

The table below shows a typical developer composition 6.7V. All inventive formulas have a pH between 9.0-10.0. When mixed with 6.7V developer, the mixed pH's are between 6.2-6.4.

Developer Composition 6.7V

|   |   | CREAM | LIQUID |
|---|---|---|---|
| HYDROGEN PEROXIDE | ACTIVE COMPOUND | 4.0 | 2 |
| WATER | SOLVENT | 91.5 | 98 |
| TETRASODIUM ETIDRONATE | ACTIVE COMPOUND | 0.2 |   |
| GLYCERIN | SOLVENT | 0.5 |   |
| TRIDECETH-2 CARBOXAMIDE MEA | SURFACTANT | 0.9 |   |
| CETEARYL ALCOHOL (and) CETEARETH-25 | SURFACTANT | 2.9 |   |
| PHOSPHORIC ACID | pH ADJUSTER | QS pH 1.8 ± 0.2 |   |

Example 4

The Color Effects of the Base Dyes

The hair coloring base compositions of Formulas 1 to 7 of Example 1 and the hair coloring base compositions of Formulas a to f of Example 2 were mixed with the developer composition of Example 3 (liquid) in a 1:1 ratio to form ready-to-use hair coloring compositions. The hair coloring base compositions are identical except for the base dyes and couplers.

The mixtures were applied to sample swatches, which are commercially available. The mixtures were allowed to remain on the hair of the swatches (to process) for 20 minutes before being rinsed from the hair with water. FIG. 1. showed that different color tones when different base dyes were used. The results clearly and surprisingly demonstrated that 2-Methoxymethyl-P-Phenylenediamine yielded more vibrant colors compared to other base dyes such as toluene-2,5-diamine (And) thioglycerin.

Example 5

Tenacity Study for 2-Methoxymethyl-P-Phenylenediamine

The hair coloring base compositions Formulas 1 to 6 of Example 1 were mixed with the developer composition of Example 3 (liquid) in a 1:1 ratio to form ready-to-use hair coloring compositions. The hair coloring base compositions are identical except for the couplers.

The mixtures were applied to sample swatches, which are commercially available. The mixtures were allowed to remain on the hair of the swatches (to process) for 20 minutes before being rinsed from the hair with water. The hair swatches were subsequently washed with a standard sulfate-base hair cleansing composition. The washing and drying procedure was repeated for many cycles, i.e., the hair swatches were washed with the standard sulfate-based hair cleansing composition and subsequently dried 28 consecutive times. Color images were captured of the swatches before application, after the initial treatment with the ready-to-use hair coloring compositions, as well as after 5, 10, and 15, 20, and 28 washes.

Figure 2:
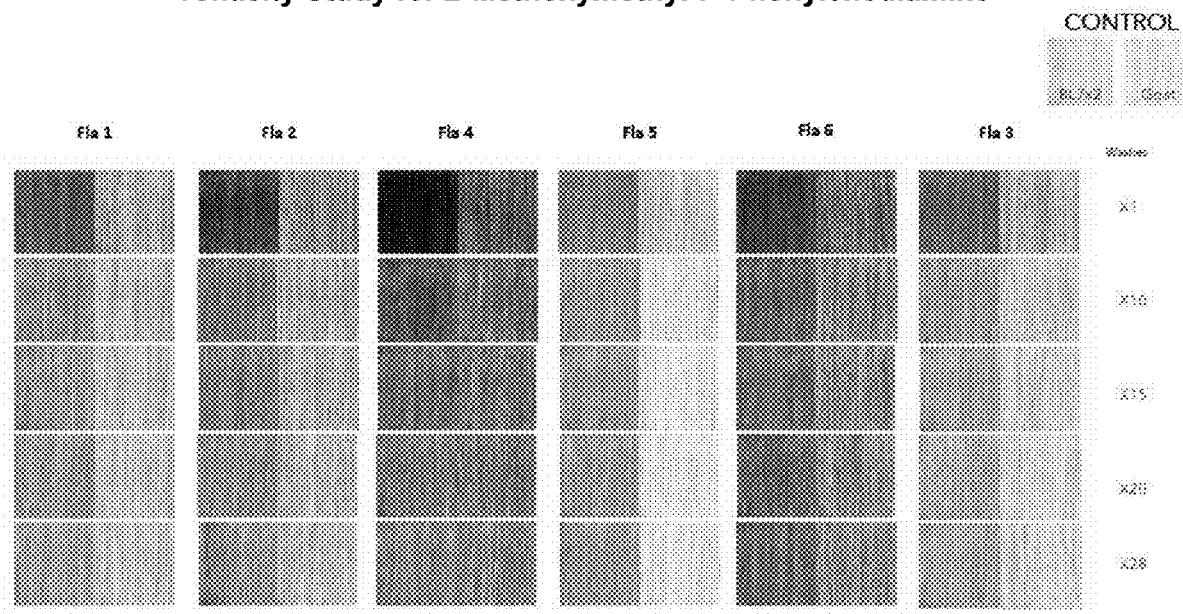
FIG. 2 is a graph showing a color tenacity study with hair colored with 2-methoxymethyl-p-phenylenediamine.

As illustrated in FIG. 2, all tested compositions exhibited good color retention after 28 washes.

Example 6

Comparative Tenacity Study for 2-Methoxymethyl-P-Phenylenediamine Vs. Toluene-2,5-Diamine (and) Thioglycerin The hair coloring base compositions of inventive Formulas 2 and 8, and comparative Formulas (g) and (h) in the table below were mixed with the developer composition of Example 3 (liquid) in a 1:1 ratio to form ready-to-use hair coloring compositions. The hair coloring base compositions are identical to the inventive formulas in Example 1 and comparative formulas in Example 2 except for the base dyes and couplers. In all four formulas, the base dye to coupler(s) molar ratio was about 1 to 1, and the dyes and couplers concentration were adjusted to obtain similar initial color deposition.

Formulas Comparison

|  |  | F2 | F8 | F(g) | F(h) |
|---|---|---|---|---|---|
| OXIDATIVE DYE PRECURSOR | 2-METHOXYMETHYL-P-PHENYLENEDIAMINE | 0.4 | 0.4 |  |  |
|  | TOLUENE-2,5-DIAMINE (and) THIOGLYCERIN |  |  | 0.2 | 0.2 |
| COUPLER | 4-AMINO-2-HYDROXYTOLUENE |  | 0.2 |  | 0.1 |
|  | 5-AMINO-6-CHLORO-o-CRESOL | 0.4 | 0.2 | 0.3 | 0.2 |

* The composition "F2," "F8," "F(g)," and "F(h)" are abbreviations for Formula 2, Formula 8, Formula (g), and Formula (h), which are also abbreviated as "Fla 2," "Fla 8," "Fla g," and "Fla h."

The mixtures were applied to sample swatches, which are commercially available. The mixtures were allowed to remain on the hair of the swatches (to process) for 20 minutes before being rinsed from the hair with water. The hair swatches were subsequently washed with a standard sulfate-base hair cleansing composition. The washing and drying procedure was repeated for many cycles, i.e., the hair swatches were washed with the standard sulfate-based hair cleansing composition and subsequently dried 28 consecutive times. Color images and color changes of the swatches were captured before application, after the initial treatment with the ready-to-use hair coloring compositions, as well as after 5, 10, and 15, 20, and 28 washes.

The color retention on the hair swatches was assessed as a function of washing using CIE L*a*b* coordinates. ΔE represents a difference in color, where a greater ΔE value represents increased removal of color or decreased retention of color. ΔE is defined by the following equation:

$$\Delta E = \sqrt{(L^* - L_0^*)^2 + (a^* - a_0^*)^2 + (b^* - b_0^*)^2}$$

where $L^*$, $a^*$, and $b^*$ represent values measured after a treatment, and $L_0^*$, $a_0^*$, and $b_0^*$ represent values measured before treatment(s).

Figure 3:
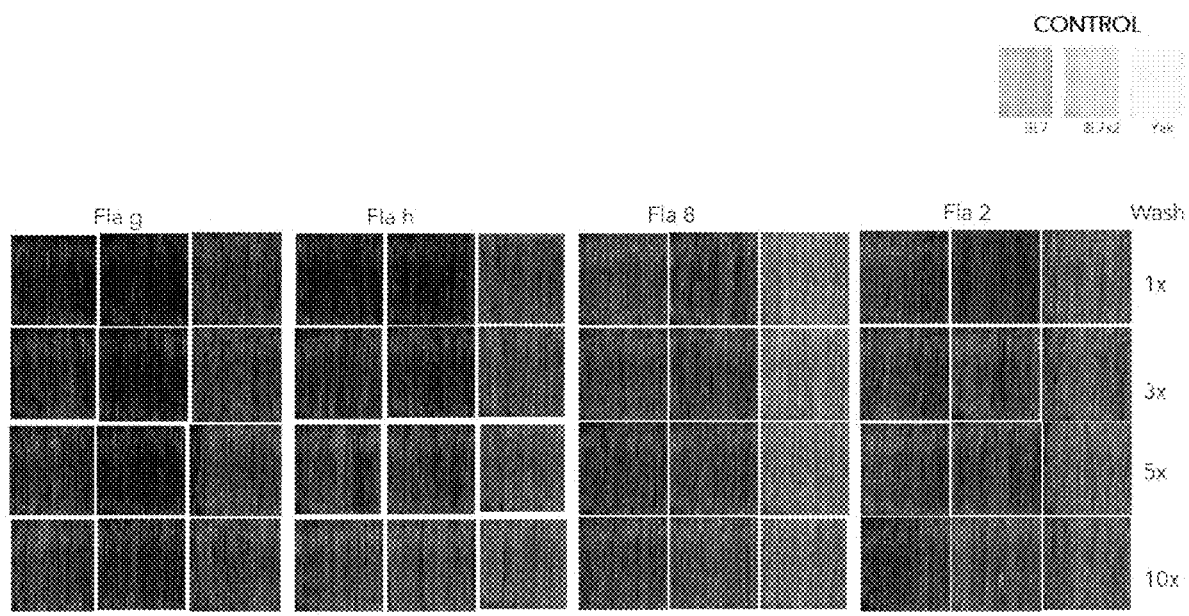
FIG. 3 is a graph showing comparative color tenacity study with hair colored with 2-methoxymethyl-p-phenylenediamine versus toluene-2,5-diamine (and) thioglycerin.
Figure 3:
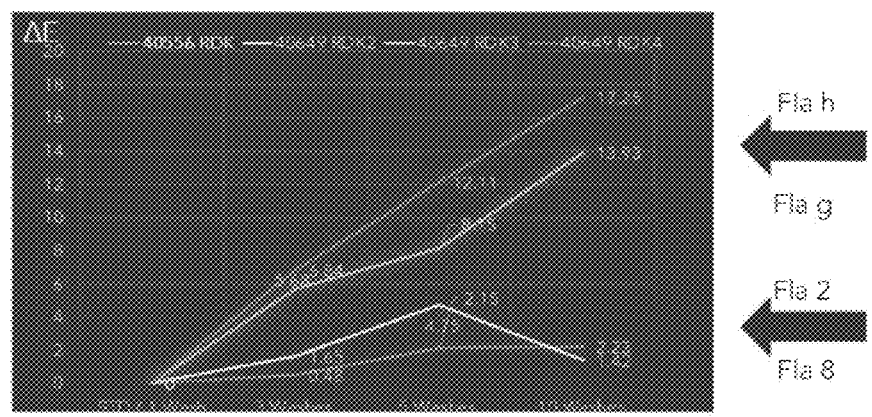

As illustrated in FIG. 3, the test compositions of inventive formulas exhibited provided significantly better color retention compared to the comparative formulas.

Example 7

Comparative Toning and Neutralizing Study for 2-Methoxymethyl-P-Phenylenediamine E 6 Vs. Toluene-2,5-Diamine (and) Thioglycerin The hair coloring base compositions of inventive Formulas 9 and 10, and comparative Formulas (i) and (j) in the table below were mixed with the developer composition of Example 3 in a 1:1 ratio to form ready-to-use hair coloring compositions.

The hair coloring base compositions the table below are identical to the inventive formulas in Example 1 and comparative formulas in Example 2 except for the base dyes and couplers. In all four formulas, the base dye to coupler(s) molar ratio was about 1 to 1.

Formulas Comparison

|  |  | F(i) | F(j) | F9 | F10 |
|---|---|---|---|---|---|
| OXIDATIVE DYE PRECURSOR | 2-METHOXYMETHYL-P-PHENYLENEDIAMINE |  |  | 0.2 | 0.2 |
|  | TOLUENE-2,5-DIAMINE (and) THIOGLYCERIN | 0.1 | 0.1 |  |  |
| COUPLER | 2,4-DIAMINOPHENOXYETHANOL HCl | 0.02 | 0.01 |  |  |
|  | 4-AMINO-2-HYDROXYTOLUENE | 0.04 | 0.1 |  |  |
|  | m-AMINOPHENOL | 0.02 | 0.01 |  |  |
|  | 5-AMINO-6-CHLORO-o-CRESOL |  |  | 0.1 | ≤0.1 |
|  | 1-NAPHTHOL |  |  | 0.1 | 0.1 |

* The composition "F(i)," "F(j)," "F9," and "F10" are abbreviations for Formula (i), Formula (j), Formula 9, and Formula 10, which are also abbreviated as "Fla i," "Fla j," "Fla 9," and "Fla 10."

The mixtures were applied to sample swatches, which are commercially available. The mixtures were allowed to remain on the hair of the swatches (to process) for 20 minutes before being rinsed from the hair with water. The hair swatches were subsequently washed with a standard sulfate-base hair cleansing composition. The washing and drying procedure was repeated for many cycles, i.e., the hair swatches were washed with the standard sulfate-based hair cleansing composition and subsequently dried 30 consecutive times. Color images, delta E and delta B values of the swatches were measured before application, after the initial treatment with the ready-to-use hair coloring compositions, as well as after 5, 10, and 15, 20, 25, and 30 washes.

Figure 4:
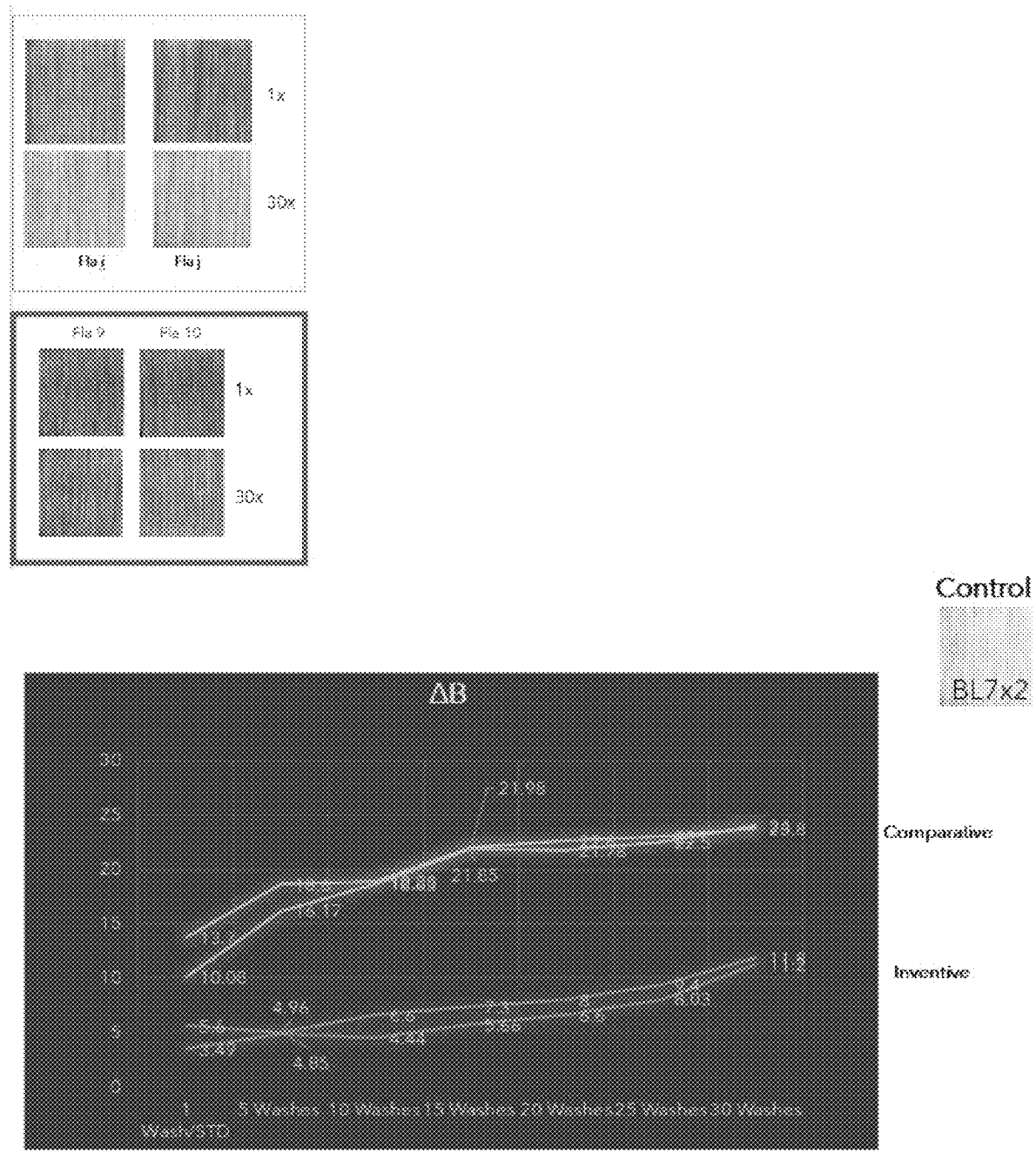
FIG. 4 is a graph showing the results of a comparative toning and neutralizing study on hair colored with 2-methoxymethyl-p-phenylenediamine versus toluene-2,5-diamine (and) thioglycerin.
Figure 5:
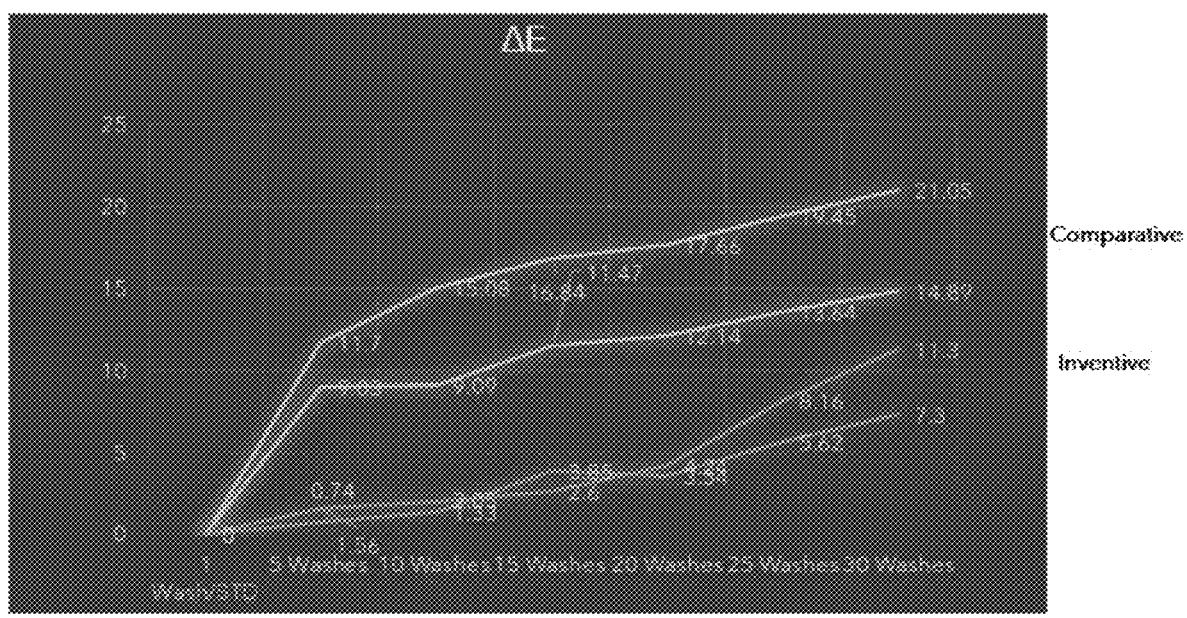
FIG. 5 is a graph showing the results of a comparative toning and neutralizing study on hair colored with 2-methoxymethyl-p-phenylenediamine versus toluene-2,5-diamine (and) thioglycerin.

Delta B value represents color change from blueness to yellowness. i.e., $\Delta b^* = b^* - b_0^*$ as described in Example 6. The higher the delta B-Value, the higher the yellowness. Lower delta B value means more neutralizing As showed in FIG. 4 and FIG. 5, the test inventive formulas have both lower Delta B and delta E after 30 washes compared to the comparative formulas.

Example 8

Hair Coloring Base Compositions

|  |  |  | J | K | L | M | N | O | P |
|---|---|---|---|---|---|---|---|---|---|
| a) |  | 2-METHOXYMETHYL-P-PHENYLENEDIAMINE | 0.3 | 0.2 | 0.2 | 0.2 | 0.2 | 0.2 | 0.2 |
| b) |  | Couplers [1] | 0.3 | 0.2 | 0.2 | 0.2 | 0.2 | 0.2 | 0.2 |
| c) |  | ETHANOLAMINE | 0.4 | 0.4 | 0.2 | 0.3 | 0.3 | 0.2 | 0.3 |
| d) |  | OLEYL, LAURYL, MYRISTYL, AND/OR CETYL ALCOHOL | 8.5 | 8.5 | 8.5 | 0-15 | | | |
| e) | Nonionic | PEG-4 RAPESEEDAMIDE DECETH-3, POLOXAMER 338, LAURETH-12, LAURETH-2, OLETH-30, GLYCERYL LAURYL ETHER, TRIDECETH-2 CARBOXAMIDE MEA, AND/OR COCAMIDE MIPA | 14.6 | 14.6 | 14.5 | 20.4 | 20.4 | 20.6 | 20.6 |
|  | Anionic | LAURETH-5 CARBOXYLIC ACID, SODIUM CETEARYL SULFATE, PPG-5-CETETH-10 PHOSPHATE, AND/OR SODIUM C14-16 OLEFIN SULFONATE | 9.9 | 9.9 | 9.9 | 1.5 | 1.5 | 1.5 | 1.5 |
|  |  | Amphoteric Surfactant (COCO-BETAINE) | 0.8 | 0.8 | 0.8 |  |  |  |  |
|  |  | Total Surfactants | 24.5 | 24.5 | 24.4 | 21.9 | 21.9 | 22.1 | 22.1 |
| f) |  | DIPROPYLENE GLYCOL, HEXYLENE GLYCOL, PROPYLENE GLYCOL, ETHANOL, ISOPROPYL ALCOHOL, GLYCERIN &/OR PPG-2 BUTYL ETHER | 22 | 22 | 22 | 3.0 | 3.0 | 3 | 3 |
|  |  | Total Water-Soluble Solvent | 22 | 22 | 22 | 3 | 3 | 3 | 3 |
| h) |  | AMMONIUM THIOLACTATE SODIUM SULFITE | 0.5 | 0.5 | 0.5 | 0.1 | 0.1 | 0.1 | 0.1 |

-continued

| | | J | K | L | M | N | O | P |
|---|---|---|---|---|---|---|---|---|
| i) | PEACH KERNEL OIL AND/OR POMEGRANATE SEED OIL | | | | 0.1 | 0.1 | 0.2 | 0.1 |
| j) | POLYQUATERNIUM-6 | | | | 0.8 | 0.8 | 0.8 | 0.8 |
| | COCODIMONIUM HYDROXYPROPYL HYDROLYZED RICE PROTEIN | | | | | | 0.1 | |
| k) | CETYL HYDROXY-ETHYLCELLULOSE | | | | 0.4 | 0.4 | 0.4 | 0.4 |
| l) | PEG/PPG-4/12 DIMETHICONE | 1.5 | 1.5 | 1.5 | | | | |
| m) | IRON OXIDES, MICA, TITAN. DIOXIDE, AND/OR ULTRAMARINES | | | | | 0.4 | 0.2 | |
| | Miscellaneous [2] | ≤5 | ≤5 | ≤5 | ≤5 | ≤5 | ≤5 | ≤5 |
| g) | WATER | 39.4 | 39.5 | 40.8 | | 50-75 | | |
| | Combination of (e), (f), and (g) | 85.9 | 86 | 87.2 | | 75-95 | | |

[1] 2-amino-3-hydroxypyridine, hydroxybenzomorpholine, 2-methyl-5-hydroxyethylaminophenol, 2-methylrescorcinol, 2,4-diaminophenoxy-ethanol HCL, 5-amino-6-chloro-o-cresol, 1-naphthol, or a combination thereof.
[2] Miscellaneous ingredients, include, for example, botanical extracts, hydrated silica, phenoxyethanol, BHT, octadecyl di-t-butyl-4-hydroxydrocinnamate, potassium sorbate, sodium benzoate, benzoic acid, pentaerythrityl tetra-di-t-butyl Hydoxyhydrocinnamate, sodium citrate, silica dimethyl silylate, sodium phosphate, disodium phosphate, sodium chloride, taurine, wheat amino acids, 2-oleamido-1,3-octadecanediol, erythorbic acid, citric acid, sodium chloride, or combinations thereof.
3 Compositions A-D are the same as Compositions A-D of Example 8 and have been included for comparison with Compositions J-P.

Definitions

The term "hair" as used herein includes hair of the head, beard hair, mustache hair, eyebrow hair, eyelashes, and body hair, unless otherwise specified.

The term "beard hair" includes mustache hair, unless otherwise specified.

As used herein, the terms "comprising," "having," and "including" are used in their open, non-limiting sense.

A "hair coloring base composition" as used herein is a hair coloring composition containing one or more oxidative dye precursors and is mixed with a developer composition to form a ready-to-use hair coloring composition. A "hair coloring base composition" may also be referred to as a "hair coloring or toning base composition."

A "developer composition" as used herein is a composition containing one or more oxidizing agents, preferably a peroxide (hydrogen peroxide) and is missed with a hair coloring base composition to form a ready-to-use hair coloring composition.

A "ready-to-use hair coloring composition" is an "active" composition that includes one or more oxidative dye precursors and one or more oxidizing agents; and is formed by combining a hair coloring base composition with a developer composition.

The term "coloring hair" refers to changing the color or tone of the hair and includes lightening, lifting, or bleaching the hair.

A "composition colorant" is a compound that colors the composition but does not have an appreciable coloring effect on hair. In other words, the composition colorant is included to provide color to the composition, for example, for aesthetic appeal. It is not included to impart color to the hair. Styling gels, for example, can be found in a variety of different colors (e.g., light blue, light pink, etc.) yet application of the styling gel to the hair does not change the color of the hair.

"Oil" is used herein to refer to an organic compound insoluble in water at normal temperature (25° C.) and at atmospheric pressure (760 mmHg), i.e. it has a water solubility of less than 5% by weight, or less than 1% by weight, or less than 0.1% by weight. Oils have in their structure a chain of at least two siloxane groups or at least one hydrocarbon chain having at least 6 carbon atoms. Furthermore, oils are generally soluble in organic solvents in the same conditions of temperature and pressure, for example in chloroform, ethanol, benzene or decamethylcyclopentasiloxane. Furthermore, oils are liquid at ordinary temperature (25° C.) and at atmospheric pressure (760 mmHg). The oils preferably do not contain any carboxylic acid functions, i.e. they do not contain any —COOH or —COO— groups. As described throughout the disclosure fatty alcohols are independent from fatty compounds and oils, i.e., even if a fatty alcohol is present in the compositions of the instant disclosure, the compositions may nonetheless be free or essentially free from fatty compounds of oils (because fatty alcohols are not included in the definition of fatty compounds and oils).

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or only the fatty compound (the single fatty acid does not serve as both the emulsifier and the fatty component). Mention of "fatty acid" and "emulsifier" is set forth as merely one example for purposes of communicating intent.

The salts referred to throughout the disclosure may include salts having a counter-ion such as an alkali metal, alkaline earth metal, or ammonium counter-ion. This list of counter-ions, however, is non-limiting. All surfactants described herein include the salt form of the surfactant, to the extent a salt form exists, regardless of whether a salt is specifically denoted.

The term "treat" (and its grammatical variations) as used herein refers to the application of a composition of the present disclosure onto hair.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

All components positively set forth throughout the instant disclosure may be negatively excluded from the claims, e.g., a claimed composition may be "free," "essentially free" (or "substantially free") of one or more components that are positively set forth in the instant disclosure. As an example, silicones can optionally be included in the compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes.

The term "substantially free" or "essentially free" as used herein means that there is less than about 5% by weight of a specific material added to a composition, based on the total weight of the compositions. Nonetheless, the compositions may include less than about 1 wt. %, less than about 0.5 wt. %, less than about 0.1 wt. %, less than 0.01 wt. %, or less than 0.001 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones, for example, dimethicones, amodimethicones, and the like. Likewise, a particular composition may be free or essentially cationic surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring base composition comprising:
    (a) 2-methoxymethyl-P-phenylenediamine, and optionally one or more additional oxidative dye precursors;
    (b) one or more couplers; and
    (c) one or more alkalizing agents;
    (d) optionally, one or more fatty alcohols having from 12 to 24 carbon atoms;
    (e) about 10 to about 40 wt. % of a plurality of surfactants, the plurality of surfactants comprising:
        (e)(1) about 10 to about 35 wt. % of one or more nonionic surfactants; and
        (e)(2) about 0.1 to about 15 wt. % of one or more anionic surfactants;
    (f) one or more water-soluble organic solvents;
    (g) water; and
    (h) not more than about 10 wt. % of one or more fatty compounds other than the one or more fatty alcohols of (d);
        wherein (e), (f), and (g) are in amounts such that a combined amount of (e), (f), and (g) constitutes at least 70 wt. % of the hair coloring base composition, and
        all percentages by weight are based on a total weight of the hair coloring composition.

2. The hair coloring base composition of claim 1, wherein the plurality of surfactants of (e) are in an amount of about 15 to about 35 wt. %.

3. The hair coloring base composition of claim 1, wherein the alkalizing agent is an organic alkalizing agent.

4. The hair coloring base composition of claim 1, wherein the one or more alkalizing agents are chosen from alkanolamines.

5. The hair coloring base composition of claim 1 being free from ammonia and ammonium ions.

6. The hair coloring base composition of claim 1, wherein the composition comprises the one or more fatty alcohols of (d) in an amount of about 0.1 to about 15 wt. %.

7. The hair coloring base composition of claim 1 comprising less than 0.1 wt. % of the one or more fatty alcohols of (d).

8. The hair coloring base composition of claim 1, wherein the plurality of surfactants comprises:
    (e)(1) about 12 to about 30 wt. % of one or more nonionic surfactants;
    (e)(2) about 0.1 to about 12 wt. % of one or more anionic surfactants; and
    (e)(3) optionally, one or more amphoteric surfactants.

9. The hair coloring base composition of claim 8, wherein the plurality of surfactants includes the one or more amphoteric surfactants of (e) (3).

10. The hair coloring base composition of claim 1 having a pH ranging from about 7 to about 10.4.

11. The hair coloring base composition of claim 1, wherein at least one of the plurality of surfactants is selected from coco-betaine, ppg-5-ceteth-10 phosphate, deceth-3, lauryl alcohol, cocamide mipa, sodium c14-16 olefin sulfonate, or a combination thereof.

12. The hair coloring base composition of claim 1, wherein at least one the one or more couplers are selected from 2-methyl-5-hydroxyethylaminophenol, 2,4-diaminophenoxyethanol hcl, 4-amino-2-hydroxytoluene, 2-amino-3-hydroxypyridine, m-aminophenol, 5-amino-6-chloro-o-cresol, 1-naphthol, or combinations thereof.

13. The hair coloring base composition of claim 1, further comprising one or more miscellaneous ingredients, where at least one of the one or more miscellaneous ingredients is an amino acid selected from taurine, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine, or combinations thereof.

14. The hair coloring base composition of claim 1, further comprising one or more miscellaneous ingredients, where at least one of the one or more miscellaneous ingredients is a carboxylic acid selected from oxalic acid, malonic acid, glutaric acid, succinic acid, adipic acid, glycolic acid, citric acid, tartaric acid, malic acid, sebacic acid, maleic acid, fumaric acid, benzoic acid, citraconic acid, aconitic acid, propane-1,2,3-tricarboxylic acid, trimesic acid, or combinations thereof.

15. A ready-to-use hair coloring composition comprising a mixture of:
(i) the hair coloring base composition of claim 1; and
(ii) a developer composition comprising:
(a) one or more oxidizing agents; and
(b) water.

16. A method for making a ready-to-use hair coloring composition comprising mixing the hair coloring base composition of claim 1 with a developer composition in a weight ratio of about 1:5 to about 5:1 (hair coloring base composition: developer composition) to form a ready-to-use hair coloring composition, wherein the developer composition comprises:
(a) one or more oxidizing agents; and
(b) water.

17. A kit comprising:
(i) one or more hair coloring base compositions of claim 1; and
(ii) one or more developer compositions comprising:
(a) one or more oxidizing agents; and
(b) water;
wherein the one or more hair coloring base compositions of (i) and the one or more developer compositions of (ii) are separately contained.

18. A method for coloring hair comprising:
(i) obtaining the hair coloring base composition of claim 1;
(ii) obtaining a developer composition comprising:
(a) one or more oxidizing agents; and
(b) water;
(iii) mixing the hair coloring base composition of (i) and the developer composition of (ii) in a weight ratio of about 1:5 to about 5:1 to form a ready-to-use hair coloring composition having a pH of about 6 to about 8; and
(iv) applying the ready-to-use hair coloring composition to hair,
(v) allowing the ready-to-use hair coloring composition to remain on the hair for a period of time, wherein the period of time is less than 30 minutes; and
(vi) after the period of time has lapsed, rinsing the ready-to-use hair coloring composition from the hair.

19. The hair coloring composition of claim 1, wherein the combined amount of (e), (f), and (g) constitutes at least 80 wt. % of the hair coloring base composition.

20. The hair coloring composition of claim 1, wherein the plurality of surfactants are in an amount of at least 24 wt. %.

* * * * *